US005766909A

United States Patent [19]
Xie et al.

[11] Patent Number: 5,766,909
[45] Date of Patent: Jun. 16, 1998

[54] DNA ENCODING INDUCIBLE NITRIC OXIDE SYNTHASE

[75] Inventors: Qiao-Wen Xie, New York; Carl F. Nathan, Larchmont, both of N.Y.; Richard A. Mumford, Red Bank; Jimmy Ramos Calaycay, Clark, both of N.J.

[73] Assignee: Merck & Co., Inc., Rahway, N.J.

[21] Appl. No.: 147,812

[22] Filed: Nov. 5, 1993

Related U.S. Application Data

[63] Continuation-in-part of Ser. No. 841,641, Feb. 4, 1992, abandoned.

[51] Int. Cl.$^6$ ............................. C12N 1/21; C12N 5/10; C12N 9/02; C12N 15/53
[52] U.S. Cl. .................... 435/189; 435/240.2; 435/252.3; 435/320.1; 536/23.2
[58] Field of Search ............................. 435/69.1, 195, 435/212, 226, 228, 240.2, 252.33, 320.1, 189, 252.3; 536/23.2

[56] References Cited

U.S. PATENT DOCUMENTS 5,132,407   7/1992   Stuehr et al. ............................. 530/395

OTHER PUBLICATIONS

Kohler & Milstein, Continuous cultures of fused cells ecreting antibody of predefined specificity, (1975), Nature, 256, pp. 495–497.
Yui, Y. et al., Calmodulin–independent Nitric Oxide Synthase from Rat Polymorphonuclear Neutrophils, (1991), J. Biol. Chem., 266, pp. 3369–3371.
Bredt, D.S. et al., Cloned and expressed nitric oxide synthase structurally resembles cytochrome P–450 reductase, (1991), Nature, 351, pp. 714–718.
Yui, Y. et al., Purification of Nitric Oxide Synthase from Rat Macrophages, (1991), J. Biol. Chem., 266, pp. 12544–12547.
Ikeda, A. et al., Studies on the Generation of Ca2+/Calmodulin–independent Activity of Calmodulin–dependent Protein Kinase II by Autophosphorylation, (1991), J. Biol Chem., 266, pp. 11582–11588.
Schmidt, H. et al., Purification of asoluble isoform of guanylyl cyclase–activating–factor synthase, (1991), Proc. Nat'l. Acad. Sci. USA, 88, pp. 365–369.
Cohen, P. et al., Identification of the Ca2+–Dependent Modulator Protein As The Fourth Subunit Of Rabbit Skeletal Muscle Phosphorylase Kinase, (1978), Febs Lett., 92, pp. 287–293.
Hevel, J.M. et al., Purification of the Inducible Murine Macrophage Nitric Oxide Synthase, (1991), J. Biol. Chem., 266, pp. 22789–22791.
Kozak, M., Structural Features in Eukaryotic mRNAs That Modulate the Initiation of Translation, (1991), J. Biol. Chem., 266, pp. 19867–19870.

Stuehr, D.J. et al., Nw–Hydroxy–l–arginine is an Intermediate in the Biosynthesis of Nitric Oxide from L–Arginine, (1991), J. Biol. Chem., 266, pp. 6259–6263.
Bredt, D.S. et al., Isolation of nitric oxide synthetase, a calmodulin–requiring enzyme, (1990), Proc. Nat'l. Acad. Sci. USA, 87, pp. 682–685.
Mayer, B. et al., Purification of a Ca2+/calmodulin–dependent nitric oxide synthase from porcine cerebellum, (1990), Febs Lett., 277, pp. 215–219.
McLuckey, S.A. et al., Ion Spray Liquid Chromatography/Ion Trap Mass Spectrometry Determination of Biomolecules, (1991), Anal. Chem., 63, pp. 375–383.
Sacks, D.B. et al., Monoclonal Antibody to Calmodulin: Development, Characterization, and Comparison with Polyclonal Anti–calmodulin Antibodies, (1991), Analty. Biochem., 194, pp. 369–377.
Pollock, J.S. et al., Purification and characterization of particulate endothelium–derived relaxing factor synthase from cultured and native bovine aortic endothelial cells, (1991), Proc. Nat'l. Acad. Sci. USA, 88, pp. 10480–10484.
Stuehr, D.J. et al., Purification and characterization of the cytokine–induced macrophage nitric oxide synthase: An FAD–and FMN–containing flavoprotein, (1991), Proc. Nat'l. Acad. Sci. USA, 88, pp. 7773–7777.
O'Neil, K.T. and DeGrado, W.F., How calmodulin binds its targets: sequence independent recognition of amphiphilic a–helices, (1990), TIBS, 15, pp. 59–64.
Harper, J.F. et al., A Calcium–Dependent Protein Kinase with a Regulatory Domain Similar to Calmodulin, (1991), Science, 252, pp. 951–954.
Porter, T.D. & Kasper, C.B., Coding nucleotide sequence of rat NADPH–cytochrome P–450 oxidoreductase cDNA and identification of flavin–binding domains, (1985), Proc. Nat'l. Acad. Sci. USA, 82, pp. 973–977.
Ladant, D., Interaction of Boretella pertussis Adenlate Cyclase with Calmodulin, (1988), J. Biol.Chem., 263, pp. 2612–2618.
Stuehr, D.J. et al., Synthesis of Nitrogen Oxides from L–Arginine by Macrophase Cytosol: Requirement for Inducible and Constitutive Components, (1989), Biochem. Biophys. Res. Comm., 161, pp. 420–426.
Stuehr, D.J. et al., FAD and GSH Participate in Macrophase Synthesis of Nitric Oxide, (1990), Biochem. Biophys. Res. Comm., 168, pp. 558–565.
Geiser, J.R. et al., Can Calmodulin Function without Binding Calcium?, (1991), Cell, 65, pp. 949–959.

(List continued on next page.)

*Primary Examiner*—Dian C. Jacobson
*Attorney, Agent, or Firm*—Michael D. Yablonsky; Jack L. Tribble

[57] ABSTRACT

Complementary DNAs (cDNAs) encoding inducible nitric oxide synthase are isolated and purified from a cDNA library prepared from macrophage-like cells activated with interferon gamma and bacterial lipopolysaccharide. The full length cDNAs of at least two isoforms of the enzyme are identified and sequenced.

8 Claims, 18 Drawing Sheets

OTHER PUBLICATIONS

Ding, A.H. et al., Release of Reactive Nitrogen Intermediates and Reactive Oxygen Intermeditates from Mouse Peritoneal Macrophages, (1988), J. Immunol., 141, pp. 2407–2412.

Stuehr, D.J. and Marletta, M.A., Induction of Nitrite/Nitrate Synthesis in Murine Macrophages by BCG Infection , Lymphokines, or Interferon–y (1987), J. Immunol., 139, pp. 518–525.

Kwon, N.S. et al., Reduced Biopterin as a Cofactor in the Generation of Nitrogen Oxides by Murine Macrophages, (1989), J. Biol. Chem., 264, pp. 20496–20501.

Sharma, R.K. and Wang, J.H., Purification and Characterization of Bovine Lung Calmodulin–dependent Cyclic Nucleotide Phosphodiesterase, (1986), J. Biol. Chem., 261, pp. 14160–14166.

Schmidt, H. and Murad, F., Purification and characterization of a human NO synthase, (1991), Biochem. Biophys. Res. Comm., 181, pp. 1372–1377.

Picton, P. et al., Phosphorylase Kinase from Rabbit Skeletal Muscle: Identification of the Calmodulin–Binding Subunits, (1980), Eur. J. Biochem., 111, pp. 553–561.

MacPherson, I., (1973), Kruse & Paterson Eds Soft Agar Techniques, pp. 276–280.

Stuehr, D. J. and Marletta, M.A. Mammalian nitrate biosynthesis: Mouse macrophages produce nitrite and nitrate in response to Escherichia coli lipopolysaccharide, (1985), Proc. Nat'l. Acad. Sci. USA, 82, pp. 7738–7742.

Lee, T.D. and Vemuri, S., MacProMass: A Computer Program to Correlate Mass Spectral Data to Peptide and Protein Structures, (1990), Biomed. Environment. Mass. Spec., 19, pp. 639–645.

Young, R.A. and Davis, R.W., Efficient isolation of genes by using antibody probes, (1983), PNAS, 80, pp. 1194–1198.

Sambrook, J. et al., Molecular Cloning, A Lab. Manual, 2nd Ed., (1989), pp. 18.2–18.18.

Lee, C.C. et al, *Science* 239: 1288–1291 (1988).

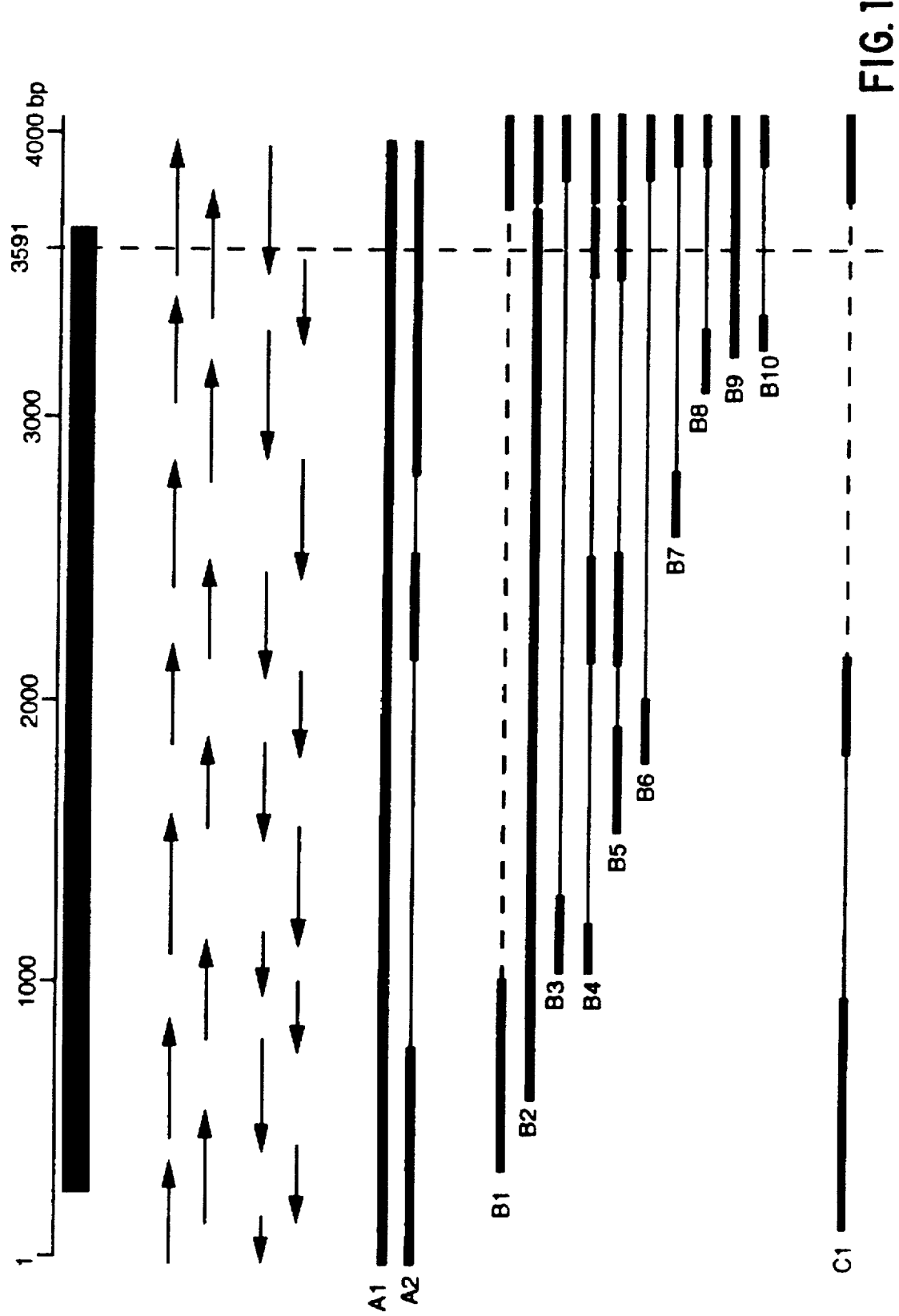

```
1    CTG GAG GGG TAT AAA TAC CTG ATG GCT GCT GCC AGG GTC ACA ACT                                    45

46   TTA CAG GGA GTT GAA GAC TGA GAC TCT GGC CCC ACG GGA CAC AGT                                    90

91   GTC ACT GGT TTG AAA CTT CTC AGC CAC CTT GGT GAA GGG ACT GAG                                    135

136  CTG TTA GAG ACA CTT CTG AGG CTC CTC ACG CTT GGG TCT TGT TCA                                    180

181  CTC CAC GGA GTA GCC TAG TCA ACT GCA AGA GAA CGG AGA ACG TTG                                    225

226  GAT TTG GAG CAG AAG TGC AAA GTC TCA GAC ATG GCT TGC CCC TGG                                    270
                                                 Met Ala Cys Pro Trp
                                                                 5

271  AAG TTT CTC TTC AAA GTC AAA TCC TAC CAA AGT GAC CTG AAA GAG                                    315
     Lys Phe Leu Phe Lys Val Lys Ser Tyr Gln Ser Asp Leu Lys Glu
                     10                  15                  20

316  GAA AAG GAC ATT AAC AAC AAC GTG AAG AAA ACC CCT TGT GCT GTT                                    360
     Glu Lys Asp Ile Asn Asn Asn Val Lys Lys Thr Pro Cys Ala Val
                     25                  30                  35

361  CTC AGC CCA ACA ATA CAA GAT GAC CCT AAG AGT CAC CAA AAT GGC                                    405
     Leu Ser Pro Thr Ile Gln Asp Asp Pro Lys Ser His Gln Asn Gly
                     40                  45                  50

406  TCC CCG CAG CTC CTC ACT GGG ACA GCA CAG AAT GTT CCA GAA TCC                                    450
     Ser Pro Gln Leu Leu Thr Gly Thr Ala Gln Asn Val Pro Glu Ser
                     55                  60                  65

451  CTG GAC AAG CTG CAT GTG ACA TCG ACC CGT CCA CAG TAT GTG AGG                                    495
     Leu Asp Lys Leu His Val Thr Ser Thr Arg Pro Gln Tyr Val Arg
                     70                  75                  80

496  ATC AAA AAC TGG GGC AGT GGA GAG ATT TTG CAT GAC ACT CTT CAC                                    540
     Ile Lys Asn Trp Gly Ser Gly Glu Ile Leu His Asp Thr Leu His
                     85                  90                  95

541  CAC AAG GCC ACA TCG GAT TTC ACT TGC AAG TCC AAG TCT TGC TTG                                    585
     His Lys Ala Thr Ser Asp Phe Thr Cys Lys Ser Lys Ser Cys Leu
                     100                 105                 110
```

FIG.2

```
586  GGG TCC ATC ATG AAC CCC AAG AGT TTG ACC AGA GGA CCC AGA GAC   630
     Gly Ser Ile Met Asn Pro Lys Ser Leu Thr Arg Gly Pro Arg Asp
                     115             120             125

631  AAG CCT ACC CCT CTG GAG GAG CTC CTG CCT CAT GCC ATT GAG TTC   675
     Lys Pro Thr Pro Leu Glu Glu Leu Leu Pro His Ala Ile Glu Phe
                     130             135             140

676  ATC AAC CAG TAT TAT GGC TCC TTT AAA GAG GCA AAA ATA GAG GAA   720
     Ile Asn Gln Tyr Tyr Gly Ser Phe Lys Glu Ala Lys Ile Glu Glu
                     145             150             155

721  CAT CTG GCC AGG CTG GAA GCT GTA ACA AAG GAA ATA GAA ACA ACA   765
     His Leu Ala Arg Leu Glu Ala Val Thr Lys Glu Ile Glu Thr Thr
                     160             165             170

766  GGA ACC TAC CAG CTC ACT CTG GAT GAG CTC ATC TTT GCC ACC AAG   810
     Gly Thr Tyr Gln Leu Thr Leu Asp Glu Leu Ile Phe Ala Thr Lys
                     175             180             185

811  ATG GCC TGG AGG AAT GCC CCT CGC TGC ATC GGC AGG ATC CAG TGG   855
     Met Ala Trp Arg Asn Ala Pro Arg Cys Ile Gly Arg Ile Gln Trp
                     190             195             200

856  TCC AAC CTG CAG GTC TTT GAC GCT CGG AAC TGT AGC ACA GCA CAG   900
     Ser Asn Leu Gln Val Phe Asp Ala Arg Asn Cys Ser Thr Ala Gln
                     205             210             215

901  GAA ATG TTT CAG CAC ATC TGC AGA CAC ATA CTT TAT GCC ACC AAC   945
     Glu Met Phe Gln His Ile Cys Arg His Ile Leu Tyr Ala Thr Asn
                     220             225             230

946  AAT GGC AAC ATC AGG TCG GCC ATC ACT GTG TTC CCC CAG CGG AGT   990
     Asn Gly Asn Ile Arg Ser Ala Ile Thr Val Phe Pro Gln Arg Ser
                     235             240             245

991  GAC GGC AAA CAT GAC TTC AGG CTC TGG AAT TCA CAG CTC ATC CGG   1035
     Asp Gly Lys His Asp Phe Arg Leu Trp Asn Ser Gln Leu Ile Arg
                     250             255             260

1036 TAC GCT GGC TAC CAG ATG CCC GAT GGC ACC ATC AGA GGG GAT GCT   1080
     Tyr Ala Gly Tyr Gln Met Pro Asp Gly Thr Ile Arg Gly Asp Ala
                     265             270             275
```

FIG.2A

| | | | | | | | | | | | | | | |
|---|---|---|---|---|---|---|---|---|---|---|---|---|---|---|
|1081|GCC|ACC|TTG|GAG|TTC|ACC|CAG|TTG|TGC|ATC|GAC|CTA|GGC|TGG|AAG|1125
| |Ala|Thr|Leu|Glu|Phe|Thr|Gln|Leu|Cys|Ile|Asp|Leu|Gly|Trp|Lys|
| | | | |280| | | |285| | | |290| | |

1126 CCC CGC TAT GGC CGC TTT GAT GTG CTG CCT CTG GTC TTG CAA GCT    1170
     Pro Arg Tyr Gly Arg Phe Asp Val Leu Pro Leu Val Leu Gln Ala
                 295             300             305

1171 GAT GGT CAA GAT CCA GAG GTC TTT GAA ATC CCT CCT GAT CTT GTG    1215
     Asp Gly Gln Asp Pro Glu Val Phe Glu Ile Pro Pro Asp Leu Val
                 310             315             320

1216 TTG GAG GTG ACC ATG GAG CAT CCC AAG TAC GAG TGG TTC CAG GAG    1260
     Leu Glu Val Thr Met Glu His Pro Lys Tyr Glu Trp Phe Gln Glu
                 325             330             335

1261 CTC GGG TTG AAG TGG TAT GCA CTG CCT GCC GTG GCC AAC ATG CTA    1305
     Leu Gly Leu Lys Trp Tyr Ala Leu Pro Ala Val Ala Asn Met Leu
                 340             345             350

1306 CTG GAG GTG GGT GGC CTC GAA TTC CCA GCC TGC CCC TTC AAT GGT    1350
     Leu Glu Val Gly Gly Leu Glu Phe Pro Ala Cys Pro Phe Asn Gly
                 355             360             365

1351 TGG TAC ATG GGC ACC GAG ATT GGA GTT CGA GAC TTC TGT GAC ACA    1395
     Trp Tyr Met Gly Thr Glu Ile Gly Val Arg Asp Phe Cys Asp Thr
                 370             375             380

1396 CAG CGC TAC AAC ATC CTG GAG GAA GTG GGC CGA AGG ATG GGC CTG    1440
     Gln Arg Tyr Asn Ile Leu Glu Glu Val Gly Arg Arg Met Gly Leu
                 385             390             395

1441 GAG ACC CAC ACA CTG GCC TCC CTC TGG AAA GAC CGG GCT GTC ACG    1485
     Glu Thr His Thr Leu Ala Ser Leu Trp Lys Asp Arg Ala Val Thr
                 400             405             410

1486 GAG ATC AAT GTG GCT GTG CTC CAT AGT TTC CAG AAG CAG AAT GTG    1530
     Glu Ile Asn Val Ala Val Leu His Ser Phe Gln Lys Gln Asn Val
                 415             420             425

1531 ACC ATC ATG GAC CAC CAC ACA GCC TCA GAG TCC TTC ATG AAG CAC    1575
     Thr Ile Met Asp His His Thr Ala Ser Glu Ser Phe Met Lys His
                 430             435             440

FIG.2B

```
1576 ATG CAG AAT GAG TAC CGG GCC CGT GGA GGC TGC CCG GCA GAC TGG    1620
    Met Gln Asn Glu Tyr Arg Ala Arg Gly Gly Cys Pro Ala Asp Trp
                        445             450             455

1621 ATT TGG CTG GTC CCT CCA GTG TCT GGG AGC ATC ACC CCT GTG TTC    1665
    Ile Trp Leu Val Pro Pro Val Ser Gly Ser Ile Thr Pro Val Phe
                        460             465             470

1666 CAC CAG GAG ATG TTG AAC TAT GTC CTA TCT CCA TTC TAC TAC TAC    1710
    His Gln Glu Met Leu Asn Tyr Val Leu Ser Pro Phe Tyr Tyr Tyr
                        475             480             485

1711 CAG ATC GAG CCC TGG AAG ACC CAC ATC TGG CAG AAT GAG AAG CTG    1755
    Gln Ile Glu Pro Trp Lys Thr His Ile Trp Gln Asn Glu Lys Leu
                        490             495             500

1756 AGG CCC AGG AGG AGA GAG ATC CGA TTT AGA GTC TTG GTG AAA GTG    1800
    Arg Pro Arg Arg Arg Glu Ile Arg Phe Arg Val Leu Val Lys Val
                        505             510             515

1801 GTG TTC TTT GCT TCC ATG CTA ATG CGA AAG GTC ATG GCT TCA CGG    1845
    Val Phe Phe Ala Ser Met Leu Met Arg Lys Val Met Ala Ser Arg
                        520             525             530

1846 GTC AGA GCC ACA GTC CTC TTT GCT ACT GAG ACA GGG AAG TCT GAA    1890
    Val Arg Ala Thr Val Leu Phe Ala Thr Glu Thr Gly Lys Ser Glu
                        535             540             545

1891 GCA CTA GCC AGG GAC CTG GCC ACC TTG TTC AGC TAC GCC TTC AAC    1935
    Ala Leu Ala Arg Asp Leu Ala Thr Leu Phe Ser Tyr Ala Phe Asn
                        550             555             560

1936 ACC AAG GTT GTC TGC ATG GAC CAG TAT AAG GCA AGC ACC TTG GAA    1980
    Thr Lys Val Val Cys Met Asp Gln Tyr Lys Ala Ser Thr Leu Glu
                        565             570             575

1981 GAG GAG CAA CTA CTG CTG GTG GTG ACA AGC ACA TTT GGG AAT GGA    2025
    Glu Glu Gln Leu Leu Leu Val Val Thr Ser Thr Phe Gly Asn Gly
                        580             585             590

2026 GAC TGT CCC AGC AAT GGG CAG ACT CTG AAG AAA TCT CTG TTC ATG    2070
    Asp Cys Pro Ser Asn Gly Gln Thr Leu Lys Lys Ser Leu Phe Met
                        595             600             605
```

FIG.2C

```
2071 CTT AGA GAA CTC AAC CAC ACC TTC AGG TAT GCT GTG TTT GGC CTT    2115
     Leu Arg Glu Leu Asn His Thr Phe Arg Tyr Ala Val Phe Gly Leu
                     610             615             620

2116 GGC TCC AGC ATG TAC CCT CAG TTC TGC GCC TTT GCT CAT GAC ATC    2160
     Gly Ser Ser Met Tyr Pro Gln Phe Cys Ala Phe Ala His Asp Ile
                     625             630             635

2161 GAC CAG AAG CTG TCC CAC CTG GGA GCC TCT CAG CTT GCC CCA ACA    2205
     Asp Gln Lys Leu Ser His Leu Gly Ala Ser Gln Leu Ala Pro Thr
                     640             645             650

2206 GGA GAA GGG GAC GAA CTC AGT GGG CAG GAG GAT GCC TTC CGC AGC    2250
     Gly Glu Gly Asp Glu Leu Ser Gly Gln Glu Asp Ala Phe Arg Ser
                     655             660             665

2251 TGG GCT GTA CAA ACC TTC CGG GCA GCC TGT GAG ACC TTT GAT GTC    2295
     Trp Ala Val Gln Thr Phe Arg Ala Ala Cys Glu Thr Phe Asp Val
                     670             675             680

2296 CGA AGC AAA CAT CAC ATT CAG ATC CCG AAA CGC TTC ACT TCC AAT    2340
     Arg Ser Lys His His Ile Gln Ile Pro Lys Arg Phe Thr Ser Asn
                     685             690             695

2341 GCA ACA TGG GAG CCA CAG CAA TAT AGG CTC ATC CAG AGC CCG GAG    2385
     Ala Thr Trp Glu Pro Gln Gln Tyr Arg Leu Ile Gln Ser Pro Glu
                     700             705             710

2386 CCT TTA GAC CTC AAC AGA GCC CTC AGC AGC ATC CAT GCA AAG AAC    2430
     Pro Leu Asp Leu Asn Arg Ala Leu Ser Ser Ile His Ala Lys Asn
                     715             720             725

2431 GTG TTT ACC ATG AGG CTG AAA TCC CAG CAG AAT CTG CAG AGT GAA    2475
     Val Phe Thr Met Arg Leu Lys Ser Gln Gln Asn Leu Gln Ser Glu
                     730             735             740

2476 AAG TCC AGC CGC ACC ACC CTC CTC GTT CAG CTC ACC TTC GAG GGC    2520
     Lys Ser Ser Arg Thr Thr Leu Leu Val Gln Leu Thr Phe Glu Gly
                     745             750             755

2521 AGC CGA GGG CCC AGC TAC CTG CCT GGG GAA CAC CTG GGG ATC TTC    2565
     Ser Arg Gly Pro Ser Tyr Leu Pro Gly Glu His Leu Gly Ile Phe
                     760             765             770
```

FIG.2D

```
2566 CCA GGC AAC CAG ACC GCC CTG GTG CAG GGA ATC TTG GAG CGA GTT    2610
     Pro Gly Asn Gln Thr Ala Leu Val Gln Gly Ile Leu Glu Arg Val
                     775             780             785

2611 GTG GAT TGT CCT ACA CCA CAC CAA ACT GTG TGC CTG GAG GTT CTG    2655
     Val Asp Cys Pro Thr Pro His Gln Thr Val Cys Leu Glu Val Leu
                     790             795             800

2656 GAT GAG AGC GGC AGC TAC TGG GTC AAA GAC AAG AGG CTG CCC CCC    2700
     Asp Glu Ser Gly Ser Tyr Trp Val Lys Asp Lys Arg Leu Pro Pro
                     805             810             815

2701 TGC TCA CTC AGC CAA GCC CTC ACC TAC TTC CTG GAC ATT ACG ACC    2745
     Cys Ser Leu Ser Gln Ala Leu Thr Tyr Phe Leu Asp Ile Thr Thr
                     820             825             830

2746 CCT CCC ACC CAG CTG CAG CTC CAC AAG CTG GCT CGC TTT GCC ACG    2790
     Pro Pro Thr Gln Leu Gln Leu His Lys Leu Ala Arg Phe Ala Thr
                     835             840             845

2791 GAC GAG ACG GAT AGG CAG AGA TTG GAG GCC TTG TGT CAG CCC TCA    2835
     Asp Glu Thr Asp Arg Gln Arg Leu Glu Ala Leu Cys Gln Pro Ser
                     850             855             860

2836 GAG TAC AAT GAC TGG AAG TTC AGC AAC AAC CCC ACG TTC CTG GAG    2880
     Glu Tyr Asn Asp Trp Lys Phe Ser Asn Asn Pro Thr Phe Leu Glu
                     865             870             875

2881 GTG CTT GAA GAG TTC CCT TCC TTG CAT GTG CCC GCT GCC TTC CTG    2925
     Val Leu Glu Glu Phe Pro Ser Leu His Val Pro Ala Ala Phe Leu
                     880             885             890

2926 CTG TCG CAG CTC CCT ATC TTG AAG CCC CGC TAC TAC TCC ATC AGC    2970
     Leu Ser Gln Leu Pro Ile Leu Lys Pro Arg Tyr Tyr Ser Ile Ser
                     895             900             905

2971 TCC TCC CAG GAC CAC ACC CCC TCG GAG GTT CAC CTC ACT GTG GCC    3015
     Ser Ser Gln Asp His Thr Pro Ser Glu Val His Leu Thr Val Ala
                     910             915             920

3016 GTG GTC ACC TAC CGC ACC CGA GAT GGT CAG GGT CCC CTG CAC CAT    3060
     Val Val Thr Tyr Arg Thr Arg Asp Gly Gln Gly Pro Leu His His
                     925             930             935
```

FIG.2E

```
3061 GGT GTC TGC AGC ACT TGG ATC AGG AAC CTG AAG CCC CAG GAC CCA   3105
     Gly Val Cys Ser Thr Trp Ile Arg Asn Leu Lys Pro Gln Asp Pro
                     940             945             950

3106 GTG CCC TGC TTT GTG CGA AGT GTC AGT GGC TTC CAG CTC CCT GAG   3150
     Val Pro Cys Phe Val Arg Ser Val Ser Gly Phe Gln Leu Pro Glu
                     955             960             965

3151 GAC CCC TCC CAG CCT TGC ATC CTC ATT GGG CCT GGT ACG GGC ATT   3195
     Asp Pro Ser Gln Pro Cys Ile Leu Ile Gly Pro Gly Thr Gly Ile
                     970             975             980

3196 GCT CCC TTC CGA AGT TTC TGG CAG CAG CGG CTC CAT GAC TCC CAG   3240
     Ala Pro Phe Arg Ser Phe Trp Gln Gln Arg Leu His Asp Ser Gln
                     985             990             995

3241 CAC AAA GGG CTC AAA GGA GGC CGC ATG AGC TTG GTG TTT GGG TGC   3285
     His Lys Gly Leu Lys Gly Gly Arg Met Ser Leu Val Phe Gly Cys
                     1000            1005            1010

3286 CGG CAC CCG GAG GAG GAC CAC CTC TAT CAG GAA GAA ATG CAG GAG   3330
     Arg His Pro Glu Glu Asp His Leu Tyr Gln Glu Glu Met Gln Glu
                     1015            1020            1025

3331 ATG GTC CGC AAG AGA GTG CTC TTC CAG GTG CAC ACA GGC TAC TCC   3375
     Met Val Arg Lys Arg Val Leu Phe Gln Val His Thr Gly Tyr Ser
                     1030            1035            1040

3376 CGG CTG CCC GGC AAA CCC AAG GTC TAC GTT CAG GAC ATC CTG CAA   3420
     Arg Leu Pro Gly Lys Pro Lys Val Tyr Val Gln Asp Ile Leu Gln
                     1045            1050            1055

3421 AAG CAG CTG GCC AAT GAG GTA CTC AGC GTG CTC CAC GGG GAG CAG   3465
     Lys Gln Leu Ala Asn Glu Val Leu Ser Val Leu His Gly Glu Gln
                     1060            1065            1070

3466 GGC CAC CTC TAC ATT TGC GGA GAT GTG CGC ATG GCT CGG GAT GTG   3510
     Gly His Leu Tyr Ile Cys Gly Asp Val Arg Met Ala Arg Asp Val
                     1075            1080            1085

3511 GCT ACC ACA TTG AAG AAG CTG GTG GCC ACC AAG CTG AAC TTG AGC   3555
     Ala Thr Thr Leu Lys Lys Leu Val Ala Thr Lys Leu Asn Leu Ser
                     1090            1095            1100
```

FIG.2F

```
3556 GAG GAG CAG GTG GAA GAC TAT TTC TTC CAG CTC AAG AGC CAG AAA    3600
     Glu Glu Gln Val Glu Asp Tyr Phe Phe Gln Leu Lys Ser Gln Lys
                         1105            1110            1115

3601 CGT TAT CAT GAA GAT ATC TTC GGT GCA GTC TTT TCC TAT GGG GCA    3645
     Arg Tyr His Glu Asp Ile Phe Gly Ala Val Phe Ser Tyr Gly Ala
                         1120            1125            1130

3646 AAA AAG GGC AGC GCC TTG GAG GAG CCC AAA GCC ACG AGG CTC TGA    3690
     Lys Lys Gly Ser Ala Leu Glu Glu Pro Lys Ala Thr Arg Leu
                         1135            1140

3691 CAG CCC AGA GTT CCA GCT TCT GGC ACT GAG TAA AGA TAA TGG TGA    3735

3736 GGG GCT TGG GGA GAC AGC GAA ATG CAA TCC CCC CAG CTC CCC TCC    3780

3781 TTC TCC TTC TCC TCC TTT GCC TCT CAC TCT TCC TTG GAG CTG AGA    3825

3826 GCA GAG AAA AAC TCA ACC TCC TGA CTG AAG CAC TTT GGG TGA CCA    3870

3871 CCA GGA GGC ACC ATG CCG CCG CTC TAA TAC TTA GCT GCA CTA TGT    3915

3916 ACA GAT ATT TAT ACT TCA TAT TTA AGA AAA CAG ATA CTT TTG TCT    3960

3961 ACT CCC AAT GAT GGC TTG GGC CTT TCC TGT ATA ATT CCT TGA TGA    4005

4006 AAA ATA TTT ATA TAA AAT ACA TTT TAT TTT AAT CAC                4041
```

FIG.2G

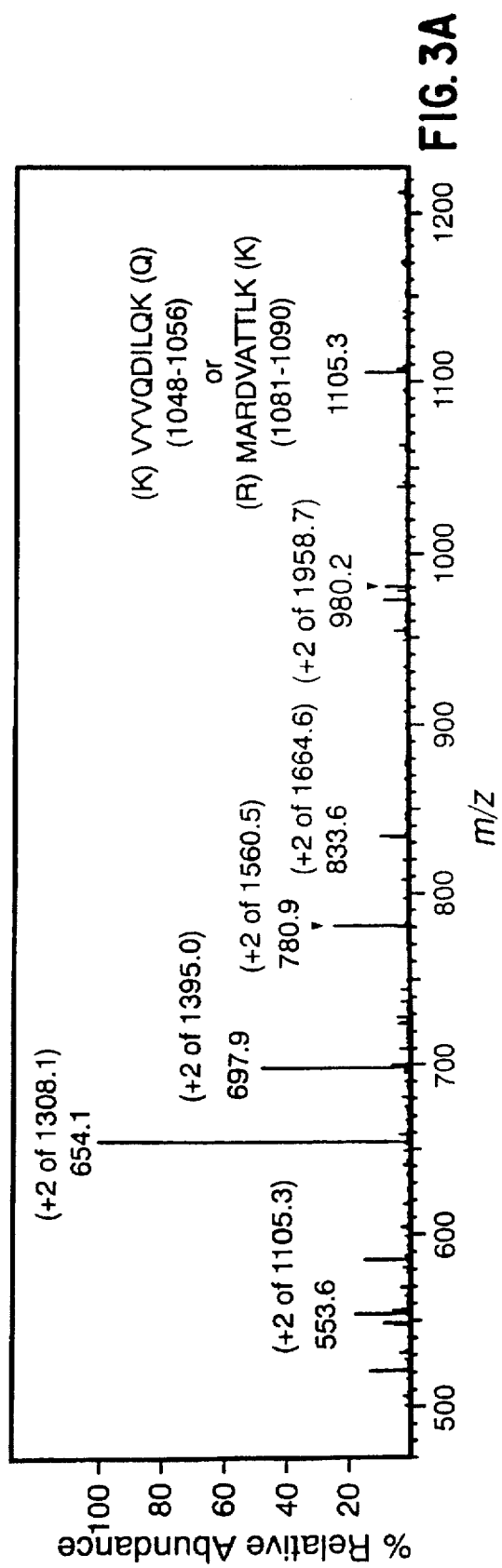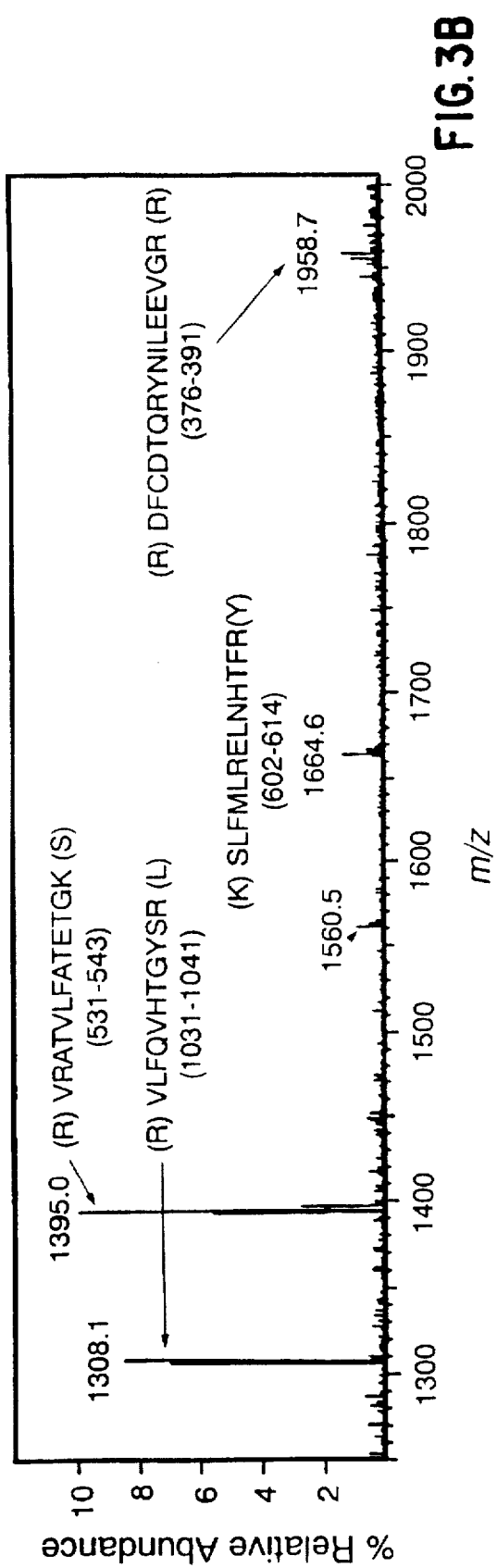
FIG. 3A
FIG. 3B

DNA NOSnew.clone13

```
           10         20         30         40         50         60
    CTGGAGGGGT ATAAATACCT GATGGCTGCT GCCAGGGTCA CAACTTTACA GGGAGTTGAA
    GACCTCCCCA TATTTATGGA CTACCGACGA CGGTCCCAGT GTTGAAATGT CCCTCAACTT 70         80         90        100        110        120
    GACTGAGACT CTGGCCCCAC GGGACACAGT GTCACTGGTT TGAAACTTCT CAGCCACCTT
    CTGACTCTGA GACCGGGGTG CCCTGTGTCA CAGTGACCAA ACTTTGAAGA GTCGTGGAA 130        140        150        160        170        180
    GGTGAAGGGA CTGAGCTGTT AGAGACACTT CTGAGGCTCC TCACGCTTGG GTCTTGTTCA
    CCACTTCCCT GACTCGACAA TCTCTGTGAA GACTCCGAGG AGTGCGAACC CAGAACAAGT 190        200        210        220        230        240
    CTCCACGGAG TAGCCTAGTC AACTGCAAGA GAACGGAGAA CGTTGGATTT GGAGCAGAAG
    GAGGTGCCTC ATCGGATCAG TTGACGTTCT CTTGCCTCTT GCAACCTAAA CCTCGTCTTC 250        260        270        280        290        300
    TGCAAAGTCT CAGACATGGC TTGCCCCTGG AAGTTTCTCT TCAAAGTCAA ATCCTACCAA
    ACGTTTCAGA GTCTGTACCG AACGGGGACC TTCAAAGAGA AGTTTCAGTT TAGGATGGTT 310        320        330        340        350        360
    AGTGACCTGA AAGAGGAAAA GGACATTAAC AACAACGTGA AGAAAACCCC TTGTGCTGTT
    TCACTGGACT TTCTCCTTTT CCTGTAATTG TTGTTGCACT TCTTTTGGGG AACACGACAA 370        380        390        400        410        420
    CTCAGCCCAA CAATACAAGA TGACCCTAAG AGTCACCAAA ATGGCTCCCC GCAGCTCCTC
    GAGTCGGGTT GTTATGTTCT ACTGGGATTC TCAGTGGTTT TACCGAGGGG CGTCGAGGAG 430        440        450        460        470        480
    ACTGGGACAG CACAGAATGT TCCAGAATCC CTGGACAAGC TGCATGTGAC ATCGACCCGT
    TGACCCTGTC GTGTCTTACA AGGTCTTAGG GACCTGTTCG ACGTACACTG TAGCTGGGCA 490        500        510        520        530        540
    CCACAGTATG TGAGGATCAA AAACTGGGGC AGTGGAGAGA TTTTGCATGA CACTCTTCAC
    GGTGTCATAC ACTCCTAGTT TTTGACCCCG TCACCTCTCT AAAACGTACT GTGAGAAGTG 550        560        570        580        590        600
    CACAAGGCCA CATCGGATTT CACTTGCAAG TCCAAGTCTT GCTTGGGGTC CATCATGAAC
    GTGTTCCGGT GTAGCCTAAA GTGAACGTTC AGGTTCAGAA CGAACCCCAG GTAGTACTTG 610        620        630        640        650        660
    CCCAAGAGTT TGACCAGAGG ACCCAGAGAC AAGCCTACCC CTCTGGAGGA GCTCCTGCCT
    GGGTTCTCAA ACTGGTCTCC TGGGTCTCTG TTCGGATGGG GAGACCTCCT CGAGGACGGA 670        680        690        700        710        720
    CATGCCATTG AGTTCATCAA CCAGTATTAT GGCTCCTTTA AAGAGGCAAA AATAGAGGAA
    GTACGGTAAC TCAAGTAGTT GGTCATAATA CCGAGGAAAT TTCTCCGTTT TTATCTCCTT
```

FIG.5

```
        730        740        750        760        770        780
CATCTGGCCA GGCTGGAAGC TGTAACAAAG GAAATAGAAA CAACAGGAAC CTACCAGCTC
GTAGACCGGT CCGACCTTCG ACATTGTTTC CTTTATCTTT GTTGTCCTTG GATGGTCGAG 790        800        810        820        830        840
ACTCTGGATG AGCTCATCTT TGCCACCAAG ATGGCCTGGA GGAATGCCCC TCGCTGCATC
TGAGACCTAC TCGAGTAGAA ACGGTGGTTC TACCGGACCT CCTTACGGGG AGCGACGTAG 850        860        870        880        890        900
GGCAGGATCC AGTGGTCCAA CCTGCAGGTC TTTGACGCTC GGAACTGTAG CACAGCACAG
CCGTCCTAGG TCACCAGGTT GGACGTCCAG AAACTGCGAG CCTTGACATC GTGTCGTGTC 910        920        930        940        950        960
GAAATGTTTC AGCACATCTG CAGACACATA CTTTATGCCA CCAACAATGG CAACATCAGG
CTTTACAAAG TCGTGTAGAC GTCTGTGTAT GAAATACGGT GGTTGTTACC GTTGTAGTCC 970        980        990       1000       1010       1020
TCGGCCATCA CTGTGTTCCC CCAGCGGAGT GACGGCAAAC ATGACTTCAG GCTCTGGAAT
AGCCGGTAGT GACACAAGGG GGTCGCCTCA CTGCCGTTTG TACTGAAGTC CGAGACCTTA 1030       1040       1050       1060       1070       1080
TCACAGCTCA TCCGGTACGC TGGCTACCAG ATGCCCGATG GCACCATCAG AGGGGATGCT
AGTGTCGAGT AGGCCATGCG ACCGATGGTC TACGGGCTAC CGTGGTAGTC TCCCCTACGA 1090       1100       1110       1120       1130       1140
GCCACCTTGG AGTTCACCCA GTTGTGCATC GACCTAGGCT GGAAGCCCCG CTATGGCCGC
CGGTGGAACC TCAAGTGGGT CAACACGTAG CTGGATCCGA CCTTCGGGGC GATACCGGCG 1150       1160       1170       1180       1190       1200
TTTGATGTGC TGCCTCTGGT CTTGCAAGCT GATGGTCAAG ATCCAGAGGT CTTTGAAATC
AAACTACACG ACGGAGACCA GAACGTTCGA CTACCAGTTC TAGGTCTCCA GAAACTTTAG 1210       1220       1230       1240       1250       1260
CCTCCTGATC TTGTGTTGGA GGTGACCATG GAGCATCCCA AGTACGAGTG GTTCCAGGAG
GGAGGACTAG AACACAACCT CCACTGGTAC CTCGTAGGGT TCATGCTCAC CAAGGTCCTC 1270       1280       1290       1300       1310       1320
CTCGGGTTGA AGTGGTATGC ACTGCCTGCC GTGGTCAACA TGTACTGGA GGTGGGTGGC
GAGCCCAACT TCACCATACG TGACGGACGG CACCAGTTGT ACGATGACCT CCACCCACCG 1330       1340       1350       1360       1370       1380
CTCGAATTCC CAGCCTGCCC CTTCAATGGT TGGTACATGG GCACCGAGAT TGGAGTTCGA
GAGCTTAAGG GTCGGACGGG GAAGTTACCA ACCATGTACC CGTGGCTCTA ACCTCAAGCT 1390       1400       1410       1420       1430       1440
GACTTCTGTG ACACACAGCG CTACAACATC CTGAGGAAG TGGGCCGAAG GATGGGCCTG
CTGAAGACAC TGTGTGTCGC GATGTTGTAG GACCTCCTTC ACCCGGCTTC CTACCCGGAC
```

FIG.5A

```
       1450        1460        1470        1480        1490        1500
GAGACCCACA  CACTGGCCTC  CCTCTGGAAA  GACCGGGCTG  TCACGGAGAT  CAATGTGGCT
CTCTGGGTGT  GTGACCGGAG  GGAGACCTTT  CTGGCCCGAC  AGTGCCTCTA  GTTACACCGA 1510        1520        1530        1540        1550        1560
GTGCTCCATA  GTTTCCAGAA  GCAGAATGTG  ACCATCATGG  ACCACCACAC  AGCCTCAGAG
CACGAGGTAT  CAAAGGTCTT  CGTCTTACAC  TGGTAGTACC  TGGTGGTGTG  TCGGAGTCTC 1570        1580        1590        1600        1610        1620
TCCTTCATGA  AGCACATGCA  GAATGAGTAC  CGGGCCCGTG  GAGGCTGCCC  GGCAGACTGG
AGGAAGTACT  TCGTGTACGT  CTTACTCATG  GCCCGGGCAC  CTCCGACGGG  CCGTCTGACC 1630        1640        1650        1660        1670        1680
ATTTGGCTGG  TCCCTCCAGT  GTCTGGGAGC  ATCACCCCTG  TGTTCCACCA  GGAGATGTTG
TAAACCGACC  AGGGAGGTCA  CAGACCCTCG  TAGTGGGGAC  ACAAGGTGGT  CCTCTACAAC 1690        1700        1710        1720        1730        1740
AACTATGTCC  TATCTCCATT  CTACTACTAC  CAGATCGAGC  CCTGGAAGAC  CCACATCTGG
TTGATACAGG  ATAGAGGTAA  GATGATGATG  GTCTAGCTCG  GGACCTTCTG  GGTGTAGACC 1750        1760        1770        1780        1790        1800
CAGAATGAGA  AGCTGAGGCC  CAGGAGGAGA  GAGATCCGAT  TTAGAGTCTT  GGTGAAAGTG
GTCTTACTCT  TCGACTCCGG  GTCCTCCTCT  CTCTAGGCTA  AATCTCAGAA  CCACTTTCAC 1810        1820        1830        1840        1850        1860
GTGTTCTTTG  CTTCCATGCT  AATGCGAAAG  GTCATGGCTT  CACGGGTCAG  AGCCACAGTC
CACAAGAAAC  GAAGGTACGA  TTACGCTTTC  CAGTACCGAA  GTGCCCAGTC  TCGGTGTCAG 1870        1880        1890        1900        1910        1920
CTCTTTGCTA  CTGAGACAGG  GAAGTCTGAA  GCACTAGCCA  GGGACCTGGC  CACCTTGTTC
GAGAAACGAT  GACTCTGTCC  CTTCAGACTT  CGTGATCGGT  CCCTGGACCG  GTGGAACAAG 1930        1940        1950        1960        1970        1980
AGCTACGCCT  TCAACACCAA  GGTTGTCTGC  ATGGACCAGT  ATAAGGCAAG  CACCTTGGAA
TCGATGCGGA  AGTTGTGGTT  CCAACAGACG  TACCTGGTCA  TATTCCGTTC  GTGGAACCTT 1990        2000        2010        2020        2030        2040
GAGGAGCAAC  TACTGCTGGT  GGTGACAAGC  ACATTTGGGA  ATGGAGACTG  TCCCAGCAAT
CTCCTCGTTG  ATGACGACCA  CCACTGTTCG  TGTAAACCCT  TACCTCTGAC  AGGGTCGTTA 2050        2060        2070        2080        2090        2100
GGGCAGACTC  TGAAGAAATC  TCTGTTCATG  CTTAGAGAAC  TCAACCACAC  CTTCAGGTAT
CCCGTCTGAG  ACTTCTTTAG  AGACAAGTAC  GAATCTCTTG  AGTTGGTGTG  GAAGTCCATA 2110        2120        2130        2140        2150        2160
GCTGTGTTTG  GCCTTGGCTC  CAGCATGTAC  CCTCAGTTCT  GCGCCTTTGC  TCATGACATC
CGACACAAAC  CGGAACCGAG  GTCGTACATG  GGAGTCAAGA  CGCGGAAACG  AGTACTGTAG
```

FIG.5B

```
            2170        2180        2190        2200        2210        2220
       GACCAGAAGC  TGTCCCACCT  GGGAGCCTCT  CAGCTTGCCC  CAACAGGAGA  AGGGGACGAA
       CTGGTCTTCG  ACAGGGTGGA  CCCTCGGAGA  GTCGAACGGG  GTTGTCCTCT  TCCCCTGCTT 2230        2240        2250        2260        2270        2280
       CTCAGTGGGC  AGGAGGATGC  CTTCCGCAGC  TGGGCTGTAC  AAACCTTCCG  GGCAGCCTGT
       GAGTCACCCG  TCCTCCTACG  GAAGGCGTCG  ACCCGACATG  TTTGGAAGGC  CCGTCGGACA 2290        2300        2310        2320        2330        2340
       GAGACCTTTG  ATGTCCGAAG  CAAACATCAC  ATTCAGATCC  CGAAACGCTT  CACTTCCAAT
       CTCTGGAAAC  TACAGGCTTC  GTTTGTAGTG  TAAGTCTAGG  GCTTTGCGAA  GTGAAGGTTA 2350        2360        2370        2380        2390        2400
       GCAACATGGG  AGCCACAGCA  ATATAGGCTC  ATCCAGAGCC  CGGAGCCTTT  AGACCTCAAC
       CGTTGTACCC  TCGGTGTCGT  TATATCCGAG  TAGGTCTCGG  GCCTCGGAAA  TCTGGAGTTG 2410        2420        2430        2440        2450        2460
       AGAGCCCTCA  GCAGCATCCA  TGCAAAGAAC  GTGTTTACCA  TGAGGCTGAA  ATCCCAGCAG
       TCTCGGGAGT  CGTCGTAGGT  ACGTTTCTTG  CACAAATGGT  ACTCCGACTT  TAGGGTCGTC 2470        2480        2490        2500        2510        2520
       AATCTGCAGA  GTGAAAAGTC  CAGCCGCACC  ACCTCCTCG   TTCAGCTCAC  CTTCGAGGGC
       TTAGACGTCT  CACTTTTCAG  GTCGGCGTGG  TGGGAGGAGC  AAGTCGAGTG  GAAGCTCCCG 2530        2540        2550        2560        2570        2580
       AGCCGAGGGC  CCAGCTACCT  GCCTGGGGAA  CACCTGGGGA  TCTTCCCAGG  CAACCAGACC
       TCGGCTCCCG  GGTCGATGGA  CGGACCCCTT  GTGGACCCCT  AGAAGGGTCC  GTTGGTCTGG 2590        2600        2610        2620        2630        2640
       GCCCTGGTGC  AGGGAATCTT  GGAGCGAGTT  GTGGATTGTC  CTACACCACA  CCAAACTGTG
       CGGGACCACG  TCCCTTAGAA  CCTCGCTCAA  CACCTAACAG  GATGTGGTGT  GGTTTGACAC 2650        2660        2670        2680        2690        2700
       TGCCTGGAGG  TTCTGGATGA  GAGCGGCAGC  TACTGGGTCA  AAGACAAGAG  GCTGCCCCCC
       ACGGACCTCC  AAGACCTACT  CTCGCCGTCG  ATGACCCAGT  TTCTGTTCTC  CGACGGGGGG 2710        2720        2730        2740        2750        2760
       TGCTCACTCA  GCCAAGCCCT  CACCTACTTC  CTGGACATTA  CGACCCCTCC  CACCCAGCTG
       ACGAGTGAGT  CGGTTCGGGA  GTGGATGAAG  GACCTGTAAT  GCTGGGGAGG  GTGGGTCGAC 2770        2780        2790        2800        2810        2820
       CAGCTCCACA  AGCTGGCTCG  CTTTGCCACG  GACGAGACGG  ATAGGCAGAG  ATTGGAGGCC
       GTCGAGGTGT  TCGACCGAGC  GAAACGGTGC  CTGCTCTGCC  TATCCGTCTC  TAACCTCCGG 2830        2840        2850        2860        2870        2880
       TTGTGTCAGC  CCTCAGAGTA  CAATGACTGG  AAGTTCAGCA  ACAACCCCAC  GTTCCTGGAG
       AACACAGTCG  GGAGTCTCAT  GTTACTGACC  TTCAAGTCGT  TGTTGGGGTG  CAAGGACCTC
```

FIG. 5C

```
        2890       2900       2910       2920       2930       2940
  GTGCTTGAAG AGTTCCCTTC CTTGCATGTG CCCGCTGCCT TCCTGCTGTC GCAGCTCCCT
  CACGAACTTC TCAAGGGAAG GAACGTACAC GGGCGACGGA AGGACGACAG CGTCGAGGGA 2950       2960       2970       2980       2990       3000
  ATCTTGAAGC CCCGCTACTA CTCCATCAGC TCCTCCCAGG ACCACACCCC CTCGGAGGTT
  TAGAACTTCG GGGCGATGAT GAGGTAGTCG AGGAGGGTCC TGGTGTGGGG GAGCCTCCAA 3010       3020       3030       3040       3050       3060
  CACCTCACTG TGGCCGTGGT CACCTACCGC ACCCGAGATG GTCAGGGTCC CCTGCACCAT
  GTGGAGTGAC ACCGGCACCA GTGGATGGCG TGGGCTCTAC CAGTCCCAGG GGACGTGGTA 3070       3080       3090       3100       3110       3120
  GGTGTCTGCA GCACTTGGAT CAGGAACCTG AAGCCCCAGG ACCCAGTGCC CTGCTTTGTG
  CCACAGACGT CGTGAACCTA GTCCTTGGAC TTCGGGGTCC TGGGTCACGG GACGAAACAC 3130       3140       3150       3160       3170       3180
  CGAAGTGTCA GTGGCTTCCA GCTCCCTGAG GACCCCTCCC AGCCTTGCAT CCTCATTGGG
  GCTTCACAGT CACCGAAGGT CGAGGGACTC CTGGGGAGGG TCGGAACGTA GGAGTAACCC 3190       3200       3210       3220       3230       3240
  CCTGGTACGG GCATTGCTCC CTTCCGAAGT TTCTGGCAGC AGCGGCTCCA TGACTCCCAG
  GGACCATGCC CGTAACGAGG GAAGGCTTCA AAGACCGTCG TCGCCGAGGT ACTGAGGGTC 3250       3260       3270       3280       3290       3300
  CACAAAGGGC TCAAAGGAGG CCGCATGAGC TTGGTGTTTG GGTGCCGGCA CCCGGAGGAG
  GTGTTTCCCG AGTTTCCTCC GGCGTACTCG AACCACAAAC CCACGGCCGT GGGCCTCCTC 3310       3320       3330       3340       3350       3360
  GACCACCTCT ATCAGGAAGA AATGCAGGAG ATGGTCCGCA AGAGAGTGCT GTTCCAGGTG
  CTGGTGGAGA TAGTCCTTCT TTACGTCCTC TACCAGGCGT TCTCTCACGA CAAGGTCCAC 3370       3380       3390       3400       3410       3420
  CACACAGGCT ACTCCCGGCT GCCCGGCAAA CCCAAGGTCT ACGTTCAGGA CATCCTGCAA
  GTGTGTCCGA TGAGGGCCGA CGGGCCGTTT GGGTTCCAGA TGCAAGTCCT GTAGGACGTT 3430       3440       3450       3460       3470       3480
  AAGCAGCTGG CCAATGAGGT ACTCAGTGTG CTCCACGGGG AGCAGGGCCA CCTCTACATT
  TTCGTCGACC GGTTACTCCA TGAGTCACAC GAGGTGCCCC TCGTCCCGGT GGAGATGTAA 3490       3500       3510       3520       3530       3540
  TGCGGAGATG TGCGCATGGC TCGGGATGTG GCTACCACAT TGAAGAAGCT GGTGGCCACC
  ACGCCTCTAC ACGCGTACCG AGCCCTACAC CGATGGTGTA ACTTCTTCGA CCACCGGTGG 3550       3560       3570       3580       3590       3600
  AAGCTGAACT TGAGCGAGGA GCAGGTGGAA GACTATTTCT TCCAGCTCAA GAGCCAGAAA
  TTCGACTTGA ACTCGCTCCT CGTCCACCTT CTGATAAAGA AGGTCGAGTT CTCGGTCTTT
```

FIG.5D

```
       3610       3620       3630       3640       3650       3660
CGTTATCATG AAGATATCTT CGGTGCAGTC TTTTCCTATG GGGCAAAAAA GGGCAGCGCC
GCAATAGTAC TTCTATAGAA GCCACGTCAG AAAAGGATAC CCCGTTTTTT CCCGTCGCGG 3670       3680       3690       3700       3710       3720
TTGGAGGAGC CCAAAGCCAC GAGGCTCTGA CAGCCCAGAG TTCCAGCTTC TGGCACTGAG
AACCTCCTCG GGTTTCGGTG CTCCGAGACT GTCGGGTCTC AAGGTCGAAG ACCGTGACTC 3730       3740       3750       3760       3770       3780
TAAAGATAAT GGTGAGGGGC TTGGGGAGAC AGCGAAATGC AATCCCCCCC AAGCCCCTCA
ATTTCTATTA CCACTCCCCG AACCCCTCTG TCGCTTTACG TTAGGGGGGG TTCGGGGAGT 3790       3800       3810       3820       3830       3840
TGTCATTCCC CCCTCCTCCA CCCTACCAAG TAGTATTGTA CTATTGTGGA CTACTAAATC
ACAGTAAGGG GGGAGGAGGT GGGATGGTTC ATCATAACAT GATAACACCT GATGATTTAG 3850       3860       3870       3880       3890       3900
TCTCTCCTCT CCTCCCTCCC CTCTCTCCCT TTCCTCCCTT CTTCTCCACT CCCCAGCTCC
AGAGAGGAGA GGAGGGAGGG GAGAGAGGGA AAGGAGGGAA GAAGAGGTGA GGGGTCGAGG 3910       3920       3930       3940       3950       3960
CTCCTTCTCC TTCTCCTCCT TTGCCTCTCA CTCTTCCTTG GAGCTGAGAG CAGAGAAAAA
GAGGAAGAGG AAGAGGAGGA AACGGAGAGT GAGAAGGAAC CTCGACTCTC GTCTCTTTTT 3970       3980       3990       4000       4010       4020
CTCAACCTCC TGACTGAAGC ACTTTGGGTG ACCACCAGGA GGCACCATGC CGCCGCTCTA
GAGTTGGAGG ACTGACTTCG TGAAACCCAC TGGTGGTCCT CCGTGGTACG GCGGCGAGAT 4030       4040       4050       4060       4070       4080
ATACTTAGCT GCACTATGTA CAGATATTTA TACTTCATAT TTAAGAAAAC AGATACTTTT
TATGAATCGA CGTGATACAT GTCTATAAAT ATGAAGTATA AATTCTTTTG TCTATGAAAA 4090       4100       4110       4120       4130       4140
GTCTACTCCC AATGATGGCT TGGGCCTTTC CTGTATAATT CCTTGATGAA AAATATTTAT
CAGATGAGGG TTACTACCGA ACCCGGAAAG GACATATTAA GGAACTACTT TTTATAAATA 4150       4160   4165
ATAAAATACA TTTTATTTTA ATCAC
TATTTTATGT AAAATAAAAT TAGTG    SEQ.ID. NO: 6
```

DNA ENCODING INDUCIBLE NITRIC OXIDE SYNTHASE

RELATED APPLICATIONS

This application is a continuation-in-part of application Ser. No. 07/841,641, filed Feb. 4, 1992 now abandoned.

This invention was made at least in part with Government support under National Institutes of Health Grant CA43610; the Government has certain rights in the invention.

BACKGROUND OF THE INVENTION

For several decades nitroglycerin has been administered to humans as a vasodilating agent in the treatment of a variety of cardiovascular diseases. Recently, it has been shown that nitroglycerin so administered is converted in the body to nitric oxide which is the pharmacologically active metabolite. Still more recently, nitric oxide has been shown to be formed enzymatically from arginine as a normal metabolite which is an important component of endothelium-derived relaxing factors (EDRFs). EDRFs are currently being intensively studied as participating in regulation of blood flow and vascular resistance. In addition to vascular endothelium, macrophages have also been shown to produce nitric oxide in the body and serves as a component of their cell killing and/or cytostatic function.

More recently it has been established that the enzyme forming nitric oxide from arginine, i.e., nitric oxide synthase, occurs in at least two distinct forms, namely the constitutive form and the inducible form.

The constitutive form is present in normal endothelial cells, neurons and some other tissues. Formation of nitric oxide by the constitutive form in endothelial cells is thought to play a role in normal blood pressure regulation. The inducible form of nitric oxide synthase has been found to be present in activated macrophages and is induced in endothelial cells and vascular smooth muscle cells, for example, by various cytokines and/or microbial products. It is thought that, in sepsis or cytokine-induced shock, overproduction of nitric oxide by the inducible form of nitric oxide synthase may play an important role in the observed life-threatening hypotension.

Considerable research effort has been expended to characterize the constitutive and inducible forms. Thus far the constitutive form has been purified to homogeneity from rat, porcine and human cerebellum, rat neutrophils and cow endothelium. Said purified constitutive form is reported to have a molecular mass as determined by sodium dodecyl sulfate polyacrylamide gel electrophoresis ranging from 150 kDa to 160 kDa, to appear to be a monomer, to require calcium and a calcium-binding protein such as calmodulin for its activation, and to be unstable (that isolated from rat cerebellum is reported to lose 50% of its enzyme activity when stored at 0° C. for 2 hours). See Bredt, et al. Proc. Natl. Acad. Sci. USA, 87: 682–683 (1990); Mayer, et al, FEBS Lett., 277: 215–219 (1991); Schmidt, cal. Proc. Natl. Acad. Sci. USA 88: 365–369 (1991); Yui, et al. J. Biol. Chem. 266: 3369–3371 (1991) and Schmidt and Murad, Biochem. Biophys. Res. Comm. 181: 1372–1377 (1991). Pollack et al., Proc. Natl. Acad. Sci. USA 88: 10480–10484 (1991).

The induction of an inducible form of nitric oxide synthase activity from mouse macrophage cell line by exposure to various cytokines and/or microbial products is reported in Stuehr, et al. J. Immunol. 139: 518–525 (1987); Ding, et al., J. Immunol. 141: 2407–2412 (1988); Drapier, et al. J. Immunol. 141: 2407–2412 (1988). Partial purification of activated mouse macrophage cell line inducible form nitric oxide synthase activity by affinity chromatography on adenosine 2',5'-bisphosphate (2',5 ADP)-Sepharose resin is reported in Stuehr, et al. Biochem. Biophys. Res. Comm. Vol. 161: No. 2, 420–426 (1989) and Kwon, et al. J. Biol. Chem. 264: 20496–20501 (1989) and Stuehr, et al. Biochem. Biophys. Res. Comm. 168: 558–565 (1990); by this method the inducible form activity is purified about 50–100-fold. For this partially purified inducible form nitric oxide synthase, nitric oxide synthesis was reported to be about 50% dependent on exogenous flavin adenine dinucleotide, about 50% dependent on glutathione, 84% dependent on tetrahydrobiopterin, 95% dependent on NADPH and 98% dependent on L-arginine; see Stuehr, et al. Biochem. Biophys. Res. Comm. 168: 558–565 (1990). Purification of mouse macrophage cell line inducible form nitric oxide synthase activity 150–200-fold by FPLC anion exchange chromatography on a Mono Q column followed by affinity chromatography on 2',5-ADP-Sepharose is reported in Stuehr, et al. J. Biol. Chem. 266: 6259–6263 (1991). Stuehr e al., have further purified murine inducible nitric oxide synthase 426-fold by sequential anion-exchange, affinity and gel filtration chromatography, Proc. Natl. Acad. Sci. USA 88: 7773–7777 (1991). Murine macrophage nitric oxide synthase has recently been purified by Hevel et al., J. Biol. Chem. 266: 22789–22791 (1991) while Yui et al., have purified nitric oxide synthase from rat macrophages, J. Biol. Chem. 266: 12544–12547 (1991). Prior to the invention herein, there is no literature report of an inducible form of a nitric oxide synthase gene.

OBJECTS OF THE INVENTION

It is, accordingly, an object of the present invention to provide novel cDNA sequences encoding inducible nitric oxide synthase (iNOS). A further object is to provide a novel cDNA encoding a biologically active inducible nitric oxide synthase. Another object is to provide expression vectors containing cDNA encoding full length iNOS and individual isoforms of the enzyme. A further object of the present invention is to provide recombinant host cells containing cDNA encoding enzymatically active iNOS. Another object is to provide monospecific antibodies which bind to iNOS, and the use of these antibodies as diagnostic reagents.

SUMMARY OF THE INVENTION

Complementary DNAs (cDNAs) encoding inducible nitric oxide synthase are isolated and purified from a cDNA library prepared from macrophage-like cells activated with interferon gamma and bacterial lipopolysaccharide. The full length cDNAs of at least two isoforms of the enzyme are identified and sequenced.

BRIEF DESCRIPTION OF THE DRAWINGS

FIG. 1 Cloned Inducible Nitric Oxide Synthase cDNAs.

FIGS. 2A–2E Panels 2A through 2E show the nucleotide and amino acid sequences of inducible nitric oxide synthase.

FIGS. 5A–5E The full length nucleotide sequence for an iNOS-encoding cDNA having the complete 3'-untranslated region is shown in Panels 5A through 5E.

DETAILED DESCRIPTION

Figure 3C:
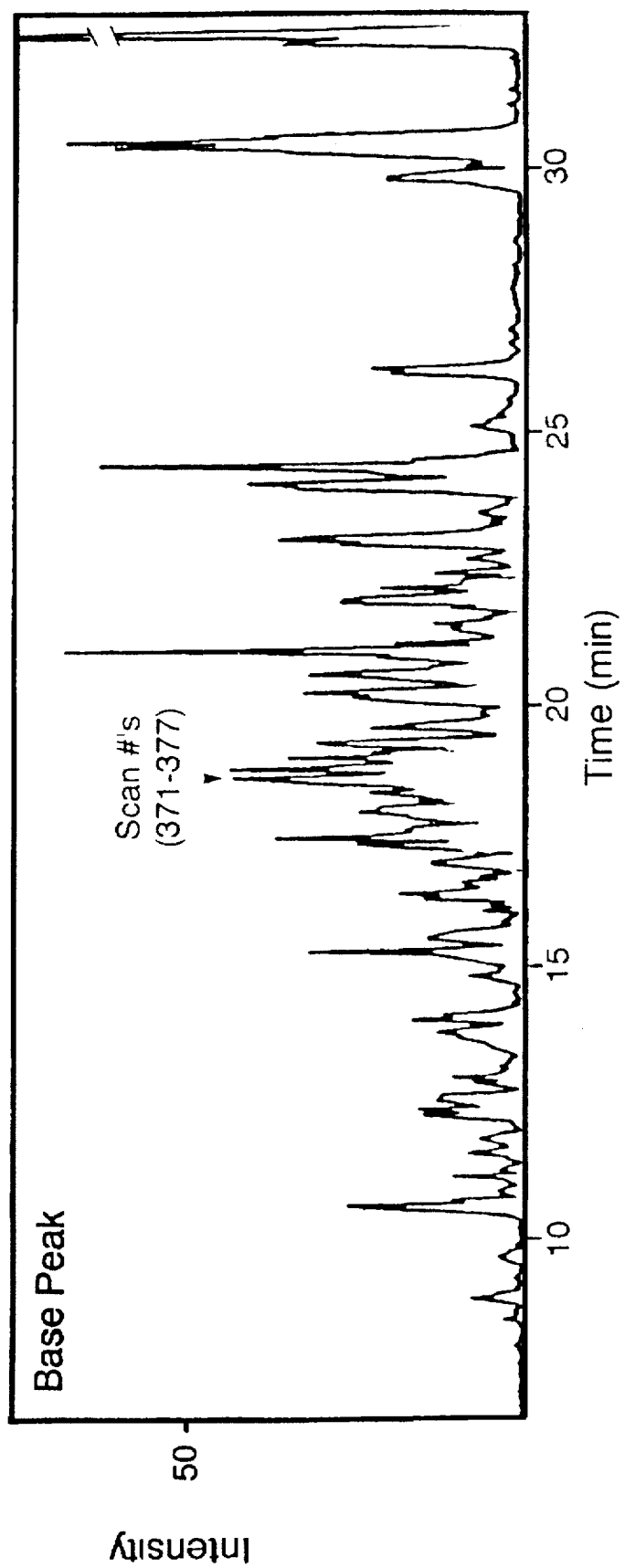
FIG. 3 Liquid chromatography-mass spectrometry analysis of a tryptic digest of inducible nitric oxide synthase is shown.

The present invention relates to unique cDNA encoding inducible nitric oxide synthase (iNOS) which is isolated and purified from macrophages, macrophage like cells and macrophage cell lines. Isolated and purified inducible NOS, as used herein, refers to an enzyme which in combination with cofactor(s) results in the generation of nitric oxide from L-arginine. The cofactors include, but are not limited to, NADPH and FMN and tetrahydrobiopterin. Other acceptable cofactors have been described by Stuehr, et al., Biochem. Biophys. Res. Comm. 168: 228–565 (1990). Enzyme activity is evaluated according to an assay described by Stuehr et al., Proc. Natl. Acad. Sci. USA 88: 7773–7777 (1991). Enzymatically active refers to a protein which can catalyze the formation of nitric oxide and is capable of being induced in macrophage like cells and other cell types. Macrophage is defined herein as a cell of the mononuclear phagocytic system and includes both fixed and circulating phagocytic cells. It is also within the scope of this invention that iNOS cDNA or gene may be isolated from other phagocytic cells following induction with interferon gamma (IFNγ) and bacterial lipopolysaccharide (LPS). Although the iNOS cDNA of this invention is described as being isolated from mouse cells, the same or substantially similar iNOS may be isolated from other mammalian cells, including human cells. Indeed, recent experiments have shown that a unique human brain cDNA segment (PCR product) which encodes a partial sequence of human cNOS has a deduced amino acid sequence that is very similar to the rat deduced sequence as shown in Bredt at al., Nature 351: 714–718 (1991). Of the approximately 220 human cNOS amino acids characterized there were only three residues which were different. This indicates that human iNOS will have an amino acid sequence substantially similar to mouse iNOS even though the nucleotide sequences may not have equivalent similarities.

Macrophage cells may be obtained from mammalian species or cell lines such as the mouse cell line RAW 264.7. The RAW 264.7 cell line and others are available from the American Type Culture Collection, Bethesda, Maryland. Macrophage cells, either cell lines or primary isolates are collected by washing with an appropriate culture medium (e.g. RPMI 1640 or Eagle's Medium), recovering the cell pellet (e.g. by centrifugation), suspending the recovered cell pellet in appropriate culture medium (e.g. RPMI 1640 containing 10% heat-inactivated fetal calf serum and 2 mg/100 ml of gentamicin sulfate), culturing and recovering cells.

Once the primary cells or cell line is obtained or prepared, it is readily cultured at 37° C., 5% $CO_2$ in appropriate culture medium, e.g. in Eagle's Medium (a modification) or RPMI 1640, supplemented with L-glutamine, penicillin, streptomycin and 8% bovine calf serum. When the cell density reaches approximately $10^6$ cells per ml, the cultured cells are ready for activation to induce nitric oxide synthase activity.

The activation is carried out by adding cytokine and/or microbial product inducing agent(s) and culturing for sufficient time to culture activated cells which are harvested and formed into a suspension of activated cells. In a preferred activation method the combination of inducing agents, recombinant mouse interferon gamma (about 100 units/ml) and *Escherichia coli* lipopolysaccharide (about 2 μg/ml), are added and the admixture is maintained for about 10–12 hours before harvesting of the activated cells.

Inducible nitric oxide synthase is then freed from the cells by lysis, e.g. by freeze-thawing in the presence of protease inhibitors, and lysate fraction containing said flavoprotein is recovered, e.g. as the supernatant from centrifugation of the lysate and is readily stored at −80° C.

The purified inducible nitric oxide synthase product herein is obtained from lysate fraction by three successive chromatography steps, a first chromatography step based on charge interaction, a second chromatography step based on cofactor specificity and a third chromatography step based on molecular mass.

A suitable buffer for use in each of the chromatography steps is about 20 mM—1,3-bis|tris(hydroxymethyl) methylaminopropane (about pH 7.2) containing about 5 mM L-arginine, about 3 mM dithiothreitol, about 2 mM flavin adenine dinucleotide, about 1 mU tetrahydrobiopterin |(6RS)-2-amino-4-hydroxy-6- (L-erythro-1,2-dihydroxypropyl)-5,6,7,8-tetrahydropteridine|, and about 10% (vol/vol) glycerol.

Any of a variety of procedures may be used to molecularly clone iNOS cDNA. These methods include, but are not limited to, direct functional expression of the iNOS cDNA following the construction of an iNOS-containing cDNA library in an appropriate expression vector system. Another method is to screen an iNOS-containing cDNA library constructed in a bacteriophage or plasmid shuttle vector with a labelled oligonucleotide probe designed from the amino acid sequence of the iNOS subunits. The preferred method consists of screening an iNOS-containing cDNA library with monospecific rabbit antibody.

It will be readily apparent to those skilled in the art that other types of libraries, as well as libraries constructed from other cells or cell types, may be useful for isolating iNOS-encoding DNA. Other types of libraries include, but are not limited to, cDNA libraries derived from other cells or cell lines other than RAW 264.7 cells, and genomic DNA libraries.

It will also be readily apparent to those skilled in the art that suitable cDNA libraries may be prepared from cells or cell lines which have iNOS activity. The selection of cells or cell lines for use in preparing a cDNA library to isolate iNOS cDNA may be done by first measuring cell associated iNOS activity using the assay described fully below. Preparation of cDNA libraries can be performed by standard techniques well known in the art. Well known cDNA library construction techniques can be found for example, in Maniatis et al., Molecular Cloning: A Laboratory Manual (Cold Spring Harbor Laboratory, Cold Spring Harbor, N.Y., 1982).

It is also readily apparent to those skilled in the art that DNA encoding iNOS may also be isolated from a suitable genomic DNA library. Construction of genomic DNA libraries can be performed by standard techniques well known in the art. Well known genomic DNA library construction techniques can be found in Maniatis et al., J. in Molecular Cloning: A Laboratory Manual (Cold Spring Harbor Laboratory, Cold Spring Harbor, N.Y., 1982).

In order to clone the iNOS gene by the preferred method, RAW 264.7 are grown and activated as previously described with the activation taking place for 4 hr. Poly(A)-rich RNA with oligo-dT as a primer is used to prepare a cDNA library in the Uni ZAP-XR unidirectional vector (Stratagene). The cDNA library is screened with iNOS monospecific antibody.

Monospecific antibodies reactive with iNOS are purified from mammalian antisera containing antibodies reactive against the enzyme or are prepared as monoclonal antibodies reactive with the enzyme using the technique of Kohler and Milstein, Nature 256: 495–497 (1975). Monospecific antibody as used herein is defined as a single antibody species or multiple antibody species with homogeneous binding characteristics for iNOS. Homogeneous binding as used herein refers to the ability of the antibody species to bind to a specific antigen or epitope, such as those associated with iNOS, as described herein.

Enzyme specific antibodies are raised by immunizing animals such as mice, guinea pigs, rabbits, goats, horses and the like, with rabbits being preferred, with an appropriate concentration of iNOS either with or without an immune adjuvant. Preimmune serum is collected prior to the first immunization. Each animal receives between about 0.1 µg and about 1000 µg of the enzyme associated with an acceptable immune adjuvant. Such acceptable adjuvants include, but are not limited to, Freund's complete, Freund's incomplete, alum-precipitate, water in oil emulsion containing *Corynebacterium parvum* and tRNA. The initial immunization consisted of the enzyme in, preferably, Freund's complete adjuvant at multiple sites either subcutaneously (SC), intraperitoneally (IP) or both. Each animal is bled at regular intervals, preferably weekly, to determine antibody titer. The animals may or may not receive booster injections following the initial immunization. Those animals receiving booster injections are generally given an equal amount of the enzyme in Freund's incomplete adjuvant by the same route. Booster injections are given at about three week intervals until maximal titers are obtained. At about 10–14 days after each booster immunization or about biweekly after a single immunization, the animals are bled, the serum collected, aliquoted and stored at about –20° C.

Monoclonal antibodies (mAb) reactive with iNOS are prepared by immunizing inbred mice, preferably BALB/c, with the iNOS enzyme. The mice are immunized by the IP or SC route with about 0.1 µg to about 10 µg, preferably about 1 µg, of iNOS in about 0.5 ml buffer or saline incorporated in an equal volume of an acceptable adjuvant, as discussed above. Freund's complete adjuvant is preferred. The mice receive an initial immunization on day 0 and are rested for about 3 to about 30 weeks. Immunized mice are given one or more booster immunizations of about 0.1 to about 10 µg of the enzyme in a buffer solution such as phosphate buffered saline by the intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions which will allow the formation of stable hybridomas. Fusion partners may include, but are not limited to: mouse myelomas P3/NS1/Ag 4-1; MPC-11; S-194 and Sp 2/0, with Sp 2/0 being preferred. The antibody producing cells and myeloma cells are fused in polyethylene glycol, about 1000 mol. wt., at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected from growth positive wells on about days 14, 18 and 21 and are screened for antibody production by an immunoassay such as solid phase immunoradioassay (SPIRA) using the iNOS as the antigen. The culture fluids are also tested in the Ouchterlony precipitation assay to determine the isotype of the mAb. Hybridoma cells from antibody positive wells are cloned by a technique such as the soft agar technique of MacPherson, Soft Agar Techniques, in Tissue Culture Methods and Applications, Kruse and Paterson, Eds., pgs. 276–280, Academic Press, 1973.

Monoclonal antibodies are produced in vivo by injecting pristane primed BALB/c mice, approximately 0.5 ml per mouse, with about $2 \times 10^6$ to about $6 \times 10^6$ hybridoma cells about 4 days after priming. Ascites fluid is collected at approximately 8–12 days after cell transfer and the monoclonal antibodies are purified by techniques known in the art.

In vitro production of anti-iNOS mAb is carried out by growing the hybridoma in DMEM containing about 2% fetal calf serum to obtain sufficient quantities of the specific mAb. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques which are well known in the art. Similar assays are used to detect the presence of iNOS in body fluids or tissue and cell extracts.

It is readily apparent to those skilled in the art that the above described methods for producing monospecific antibodies may be utilized to produce antibodies specific for iNOS polypeptide fragments, of full-length biologically active enzyme.

Anti-iNOS antiserum is raised by injecting at least one rabbit with about 90 µg 130-kDa iNOS purified from activated RAW 264.7 cells as described by above and by Stuehr et al., Proc. Natl. Acad. Sci. USA 88: 7773–7777 (1991) and emulsified with Freund's complete adjuvant. The animals are boosted with 2 injections of incomplete Freund's adjuvant containing about 45–50 µg each of iNOS that is purified as above and additionally by isolation of the 130-kDa region on SDS-PAGE. Anti-iNOS IgG was purified on immobilized recombinant protein G (Pierce), adsorbed with *E. coli*, and used to screen the cDNA library by techniques well known in the art.

The RAW 264.7 murine macrophage cell line is activated with rIFNγ (100 U/ml; Genentech) and LPS (2 µg/ml) for 4 h. Poly(A)-rich RNA with oligo-dT as a primer is used to prepare a cDNA library in the Uni ZAP-XR unidirectional vector following the manufactur's instructions (Stratagene). The antibody identified 13 clones among $5 \times 10^4$ phages in the cDNA library prepared from the activated RAW 264.7 cells (FIG. 1). The cDNA inserts in these clones contained overlapping portions of the coding region. Clones A1, A2 and B1 included the ATG initiation codon within a consensus initiation sequence (GACATGG). Kozak, J. Biol. Chem. 266: 19867–19870 (1991). The 3' untranslated regions of clones A1 and A2 are mutually identical, but differed from the mutually similar 3' untranslanted regions sequenced in clones B1–B11. Clones A1 and A2 encode a protein 22 amino acid residues shorter at the COOH-terminus, whose last 10 amino acid residues differ completely from the COOH-terminus encoded by clones of the B series. This suggests the existence of at least two isoforms of iNOS mRNA, probably generated by alternative splicing. At the protein level, the sequence was confirmed for peptides that corresponded to 22 of the 34 $NH_2$-terminal residues encoded by the clones A1, A2 and B1 to Arg704 encoded by the B clones, where the A clones have Ser704; and to 32 residues of the B clones' longer COOH-terminus, but not to the shorter COOH-terminus. Therefore, for the nucleotide and deduced amino acid sequences as shown in FIG. 2, the $NH_2$-terminus is contributed by the A1, A2 and B1 clones, and the rest of the molecule by the remaining B clones, totalling about 1144 amino acids with a predicted molecular mass of about 130,556. This constitutes the long isoform of iNOS. Isoform as used herein refers to two or more molecular forms of functionally related proteins that differ only slightly in their structure.

The nucleotide sequence of the short isoform is identical with the long isoform from nucleotide 1 through nucleotide 3591 as depicted in FIG. 2 except for nucleotide no. 2367 (T in short form; G in long form). The nucleotide and amino acid sequence of the carboxyl terminus of the short form is shown below beginning at nucleotide 3592 and running through 3621, see the following table.

TABLE 1

| GCC | TCG | GTC | CTC | CTC | AAC | CCA | CAG | AAT | AAC |
|---|---|---|---|---|---|---|---|---|---|
| Ala | Ser | Val | Leu | Leu | Asn | Pro | Gln | Asn | Asn |
| 1113 | | | | | | 1120 | | | 1123 |

SEQ ID NO :1: AND :2:

The nucleic acid sequence for the carboxyl terminus of the short isoform is shown in the following table. The sequence in Table 2 is substituted for the sequence begining at nucleotide 3591 and concluding at nucleotide 4165 of FIGS. 2 and 5 which is the long isoform.

TABLE 2

| GGCCTCGGTC | CTCCTCAACC | CACAGAATAA | CTAAGTCCTG | 40 |
|---|---|---|---|---|
| CTGGATGGGA | CAGAGTGGCG | CCCAGACGTG | GGGCTCGAGG | 80 |
| CACAGACCTT | TGCCCAGTGG | AGACCACGGA | GACTAGCTCC | 120 |
| AAGAGAATTT | TGTCACGACT | AGATGAATAA | GCCGTTTGAG | 160 |
| GAATGCTCCT | ACTGCTCACT | GGAGAAGTTG | TTCTCGGTAA | 200 |
| GTTGATTCCT | CTCCACTAAG | AAATGGGAAC | TAGCCAGGTG | 240 |
| GTGGTGGCAC | ATGCCTTTAA | TCCCAGCACT | TGGGAGGCAG | 280 |
| AGGCAGGCCG | ATTCTACAAA | GTGAGTTCCA | GGACAGCCAG | 320 |
| GGCTACACAG | AGAAACCCTG | TCTCAAAAAA | TC | 352 |

SEQ ID NO :3:

The cloned iNOS cDNA obtained through the methods described above may be recombinantly expressed by molecular cloning into an expression vector containing a suitable promoter and other appropriate transcription regulatory elements, and transferred into prokaryotic or eukaryotic host cells to produce recombinant iNOS. Techniques for such manipulations are fully described in Maniatis, T. et al., supra, and are well known in the art.

Expression vectors are defined herein as DNA sequences that are required for the transcription of cloned copies of genes and the translation of their mRNAs in an appropriate host. Such vectors can be used to express eukaryotic genes in a variety of hosts such as bacteria, bluegreen algae, plant cells, insect cells and animal cells.

Specifically designed vectors allow the shuttling of DNA between hosts such as bacteria-yeast or bacteria-animal cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses. A variety of mammalian expression vectors may be used to express recombinant iNOS in mammalian cells.

Commercially available bacterial expression vectors which may be suitable for recombinant iNOS expression, include but are not limited to, pKC30 (ATCC 37286), pPLa2311 (ATCC 31694), pBR322 (ATCC 31344 and 37017), ptac12 (ATCC 37138), λgt11 (ATCC 37194), pAS1 (ATCC39262), pLC24, pSB226, SV40 and pKK 223-3.

Commercially available mammalian expression vectors which may be suitable for recombinant iNOS expression, include but are not limited to, pBC12BI (ATCC 67617), pMC1neo (Stratagene), pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), pcDNAI (Invitrogen Corp.) and λZD35 (ATCC 37565).

DNA encoding iNOS may also be cloned into an expression vector for expression in a recombinant host cell. Recombinant host cells may be prokaryotic or eukaryotic, including but not limited to bacteria, yeast, mammalian cells including but not limited to cell lines of human, bovine, porcine, monkey and rodent origin, and insect cells including but not limited to drosophila derived cell lines. Cell lines derived from mammalian species which may be suitable and which are commercially available, include but are not limited to, CV-I (ATCC CCL 70), COS-I (ATCC CRL1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-I (ATCC CCL26), 293 (ATCC CRL 1573) and MRC-5 (ATCC CCL 171). The bacterial cell most used for expression of recombinant protein is *Escherichia coli*. There are various strains of *E. coli* available and are well known in the art.

The expression vector may be introduced into host cells via any one of a number of techniques including but not limited to transformation, transfection, protoplast fusion, and electroporation. The expression vector-containing cells are clonally propagated and individually analyzed to determine whether they produce iNOS protein. Identification of iNOS expressing host cell clones may be done by several means, including but not limited to immunological reactivity with anti-iNOS antibodies, and the presence of host cell-associated iNOS activity. Expression of iNOS DNA may also be performed using in vitro produced synthetic mRNA. Synthetic mRNA can be efficiently translated in various cell-free systems, including but not limited to wheat germ extracts and reticulocyte extracts, as well as efficiently translated in cell based systems, including but not limited to microinjection into frog oocytes.

Levels of iNOS protein in host cells is quantitated by immunoaffinity and/or ligand affinity techniques. Induced iNOS-specific affinity beads or iNOS-specific antibodies are used to isolate $^{35}$S-methionine labelled or unlabelled iNOS protein. Labelled iNOS protein is analyzed by SDS-PAGE. Unlabelled iNOS protein is detected by Western blotting, ELISA or RIA assays employing iNOS specific antibodies by processes known in the art.

Following expression of iNOS in a recombinant host cell, iNOS protein may be recovered to provide iNOS in active form, capable of carrying out specific enzymatic activity. Several iNOS purification procedures are available and suitable for use. As described for purification of iNOS from natural sources, recombinant iNOS may be purified from cell lysates and extracts, or from conditioned culture medium, by various combinations of, or individual application of ion exchange chromatography, affinity chromatography and gel filtration chromatography. A preferred method of isolating recombinant iNOS is as follows. The first chromatography step was a prepacked Mono Q HR 10/10. The chromatography column for the second chromatography step was a 5/100-mm column containing adenosine 2',5'-bisphosphate-Sepharose resin. The column for the third chromatography step was a prepacked TSK G3000 SW (7.5×600 mm) column. All chromatography for purification was carried out with the columns at room temperature. Eluant fractions from chromatography were collected into plastic tubes on ice. The buffer for all chromatography steps was 20 mM 1,3-bis[tris(hydroxymethyl)methylamino] propane (pH 7.2) containing 5 mM L-arginine, 3 mM dithiothreitol, 2 mM flavin adenine dinucleotide, 1 mM tetrahydrobiopterin [(6R,S)-2-amino-4-hydroxy-6-(L-erythro-1,2-dihydroxypropyl) -5,6,7,8-tetrahydropteridine), and 10% (vol/vol) glycerol, except where otherwise specified. Assays for nitric oxide synthase activity were carried out under the assay conditions set forth above. In these assays nitrite concentration was measured as follows: Aliquots (50- or 100 μl) were incubated with an equal volume of Griess reagent (1% sulfanilamide/0.1% naphthylethylene diamine dihydrochloride/2.5% $H_3PO_4$) at room temperature for 10 minutes. The absorbance at 550 nm was determined in a Biotek microplate reader. $NO_2^-$—was determined using sodium nitrite as a standard. Lysed cell-free medium alone contained 0.2 to 0.3 nmol of $NO_2^-$/well; this value was determined in each experiment and subtracted from the value obtained with the synthase containing sample. Fractions were assayed in duplicate. In some cases, in making kinetic measurements, production of nitrate and nitrite (stable oxidation products of nitric oxide that accumulate quantitatively over time under the conditions used) was monitored by an automated nitrite/nitrate analyzer as described in Green, L. C., et al, Anal. Biochem. 126, 131–138 (1982). Values on activity and other properties are averages from three purifications starting with a mean of $5 \times 10^9$ cells.

Refolding of purified proteins expressed in bacteria is well known in the art. Thus, one skilled in the art will be able to isolate and purify enzymatically active iNOS.

To confirm the deduced amino acid sequence of iNOS, purified, enzymatically active iNOS was subjected to reverse phase HPLC on a $C_4$ column, digested with trypsin, and the peptides separated by reverse phase HPLC on a $C_{18}$ column. The fragments recovered in greatest abundance are sequenced by Edman degradation using procedures well know in the art. Eighteen tryptic peptides matched the deduced amino acid sequence, confirming that the cDNA encoded iNOS. However, only 9% of the predicted amino acid sequence was confirmed in this manner.

Additional conformation of the amino acid sequence is obtained by liquid chromatography-mass spectrometry (LC-MS). A tryptic digest of iNOS is separated on a $C_{18}$ packed capillary column and fed directly into the electrospray interface of a quadrupole mass spectrometer, McLuckey et al., Anal. Chem. 63: 375–383 (1991). A plot of the intensity of the most intense ion in each mass spectrum vs. time yields the base peak chromatogram shown in FIG. 3A. With few exceptions, electrospray spectra of peptides contain ions only for intact molecules. Nevertheless, the present spectra are quite complex, due to the large number of peptides in the digest and the multiplicity of charge states observed. FIG. 3B illustrates this with the mass spectrum for one base ion peak. Singly and doubly charged ions are observed for six peptides. Five of these differed by <1 mass unit from products expected from tryptic cleavage of the protein deduced from the cDNA sequence. Rarely, an observed mass corresponded to more than one possible tryptic peptide; an example is included in FIG. 3B.

A MacProMass program is used calculate values for all expected tryptic peptides, including those resulting from incomplete digestion. Mass chromatograms are generated for each expected mass. For peptides larger than 1000 daltons (Da), two or more charge states have to be present in the spectrum before an assignment is made.

Because no data are collected for m/z<500, multiply-charged ions smaller than 1000 Da are not observed. Consequently, assignments for these peptides had to be based on a single ion in the spectrum. Such assignments are made only if the ion in question can not be included in an ion series corresponding to a larger peptide. Using these criteria, assignments of tryptic peptides are made that confirmed 65% of the deduced amino acid sequence of iNOS. LC-MS analysis of an endopeptidase Asp-N digest extended the confirmation to 78% of the sequence. For these studies, enzymatic digestion of iNOS is carried out without prior reduction and alkylation. Cys residues are present in 12 of the 17 regions for which LC-MS did not provide sequence confirmation; these peptides may have been linked together.

The following examples illustrate the present invention without, however, limiting the same thereto.

EXAMPLE 1

Purification of Inducible Nitric Oxide Synthase

RAW 264.7 macrophages (American Type Culture Collection, Bethesda, Md.) were grown at 37° C., 5% $CO_2$ in 6 liters of RPMI 1640 (KC Biological Inc.) supplemented with 8% bovine calf serum (HyClone Systems), L-glutamine (584 mg/l), penicillin (50 U/Ml), and streptomycin (50 mg/ml). When cells reached a density of approximately $10^6$ cells per ml, 100 units/ml of recombinant mouse interferon-gamma (Genentech) and 2 μg/ml of *Escherichia coli* lipopolysaccharide (Sigma Chemical Co.) were added to induce nitric oxide synthase activity. After 10–12 hr, the cells were harvested by centrifugation at 4° C. and resuspended in 80 ml of ice-cold saline that contained 25 mM glucose. The yield was about $5 \times 10^9$ cells with a viability (by trypan-blue exclusion) of greater than 90%. The cells were repelleted and resuspended in 16 ml of cold $H_2O$ containing protease inhibitors (0.1 mM phenylmethylsulfonylfluoride, 5 mg/ml aprotinin, 1 mg/ml chymostatin, and 5 mg/ml pepstatin A), and then lysed by three cycles of rapid freeze-thawing. The lysate was separated by centrifugation at 100,000×g for 90 min. at 4° C. and the supernatant fluid which contained nitric oxide synthase activity was stored at about −80° C.

The supernatant fluid was chromatographed in three runs of 5 ml each on the Mono Q column in a first chromatography step at a flow rate of 2 ml/min. A programmed gradient was run from 0.12 to 1.0M NaCl to elute nitric oxide synthase activity.

The active fractions from the first chromatography step (approximately 10 ml each) were respectively used for three runs in a second chromatography step. Each run involved the following. Active fraction from a first chromatography step run was loaded directly at 0.3 ml/min onto the adenosine 2',5'-bisphosphate-Sepharose resin affinity column. After unbound protein had been eluted, the nonspecifically bound proteins were eluted with 5 ml of buffer containing 0.6M NaCl. Nitric oxide synthase activity was then eluted with 5 ml of buffer containing 8 mM NADPH.

The active fractions from the three runs of the second chromatography were pooled (15 ml) and then concentrated at 4° C. in a Centricon-30 microconcentrator (Amicon). The concentrate (300–400 µl) was washed twice with 1 ml of buffer to remove most of the residual NADPH. The sample (300–400 µl) was stored at −80° C.

The 300–400 µl sample was subjected to size exclusion gel filtration chromatography on a TSK G3000 SW column. This was carried out at 0.25 ml/min on 50 ml aliquots of the 300–400 µl sample, using column buffer supplemented with 0.2M NaCl. The protein eluted in two peaks with the first peak being nitric oxide synthase. The nitric oxide synthase flavoprotein product from the TSK G3000 SW column, i.e., purified enzyme, was estimated to have a molecular mass of between 250 and 290 kDa. This result was confirmed using a TSK G4000 SW (7.5×600 mm) column. The nitric oxide synthase product was obtained in an amount of approximately 1.5 ml. The purified enzyme could be stored at −80° C.

The amount of protein, the total activity, the specific activity, the yield percent and the purification factor were determined for the various stages to be as follows (values are averages determined on products from three purifications): For lysate supernatant, samples on average contained 198 mg protein, had a total activity of 487.2 nmol of $NO_2$— per minute, had a specific activity of 2.5 nmol of $NO_2$— per minute per mg of protein, had a yield percent of 100 and had a purification factor of 1. For nitric oxide synthase active fraction obtained from the Mono Q column, fractions on average contained 7.6 mg protein, had a total activity of 141.2 nmol $NO_2$— per minute, had a specific activity of 21.3 nmol $NO_2$— per minute per mg of protein, had a yield percent of 29% and had a purification factor of 9. For nitric oxide synthase active fraction obtained from the 2',5'-ADP-Sepharose resin column, fractions on average contained 0.27 mg protein, had a total activity of 50.0 nmol of $NO_2$— per minute, had a specific activity of 197 nmol of $NO_2$— per minute per mg of protein, had a yield percent of 10.2% and had a purification factor of 83. For purified nitric oxide synthase product obtained from the TSK G3000 column, fractions on average contained 0.04 mg protein, had a total activity of 42.4 nmol of $NO_2$— per minute, had a specific activity of 1060 nmol of $NO_2$— per minute per mg of protein, had a yield percent of 8.7 and had a purification factor of 426. Thus the nitric oxide synthase product from the TSK G3000 SW column was purified 426-fold compared to the nitric oxide synthase in the lysate supernatant. The purified nitric oxide synthase product was determined to have a specific activity of 1313 nmol of $NO_2$— plus $NO_3$— per minute per mg of enzyme when assayed in the presence of L-arginine, NADPH, tetrahydrobiopterin, flavin adenine dinucleotide and reduced thiol.

The sodium dodecyl sulfate polyacrylamide gel electrophoresis (7.5% polyacrylamide gel, 1 µg of protein per lane, silver-stained) of the purified iNOS and the molecular weight standards, rabbit muscle myosin heavy chain (200,000), *E. coli* beta-galactosidase (116,000), rabbit muscle phosphorylase b (97,400), bovine albumin (66,000), ovalbumin (45,000) and bovine carbonic anhydrase (29,000) revealed that the purified enzyme migrates as tight triplet of silver-stained protein bands (i.e. three very closely spaced bands). The purified protein had an estimated molecular mass of 125–135 kilodaltons (kDa) which has been averaged to 130 kDa. Despite the fact that there is a triplet, the tightness of the bands indicates purification to homogeneity and may indicate a minor degree of proteolysis that occurs prior to the sodium dodecyl sulfate polyacrylamide gel procedure or may reflect the expression of different isoforms. The molecular mass obtained is a denatured molecular mass (because boiling the sample in sodium dodecyl sulfate for electrophoresis denatures the protein) and is about half of that estimated for the catalytically active nitric oxide synthase on both TSK G3000 SW and TSK G4000 SW gel filtration columns. This suggests that the inducible (macrophage source) nitric oxide synthase product is catalytically active as a dimer.

EXAMPLE 2

Calmodulin Binding Capacity of Inducible Nitric Oxide Synthase

Inducible NOS was purified from activated RAW 264.7 macrophage-like cells as described in Example 1. $Ca^{++}$ was not added to any of the buffers or other reagents used for purification. No free calmodulin (CaM) should copurify with iNOS, since iNOS has a predicted pi of 7.7, binds to and elutes specifically from 2',5'-ADP-Sepharose, and has a molecular mass (Mr) of ~250–290 kDa in its dimeric form, while in contrast, CaM has a pi of 4.3, is not expected to bind to or elute specifically from 2',5'-ADP-Sepharose, and has a Mr of 16.9 kDa. Separation data suggests that iNOS purified through the first two chromatographic steps displays no peak corresponding to free CaM, and that any free CaM that might have been present at that stage should be separated widely from iNOS by the size exclusion chromatography. Nonetheless, a monoclonal ab (mAb) specific for the COOH-terminus of CaM, Sacks, et al., Analyt. Biochem. 194: 369–377 (1991), reacted with two regions in an immunoblot of purified iNOS. The lower-Mr bands co-migrated with authentic CaM; the doublet at ~130 kDa represented iNOS. Thus, iNOS appeared to have a CaM-like antigen so tightly bound that the two moieties copurified in the absence of added $Ca^{++}$. It was especially surprising that some of the CaM-like antigen remained associated with iNOS even after the enzyme was boiled and electrophoresed in sodium dodecylsulfate (SDS), a treatment that generally disrupts noncovalently associated protein complexes.

To determine if the CaM-like antigen was bound to iNOS covalently, we boiled pure iNOS in the presence of ethylenediaminetetraacetic acid (EDTA). Under these conditions, iNOS disappeared from the fluid phase and appeared in the precipitate, having lost its reactivity with anti-CaM mAb. Under the same conditions, authentic CaM, a heat-resistant protein, remained partially in solution. Likewise, when iNOS was boiled with EDTA, both the supernatant and the precipitate contained protein that comigrated with CaM and reacted with anti-CaM mAb. Furthermore, all detectable CaM-like antigen was removed from iNOS by electrophoresis in 2.5M urea with 0.9M acetic acid (pH 3). Thus, the CaM-like antigen was bound tightly to iNOS, but the attachment was noncovalent To identify the CaM-like antigen, a supernatant fluid was generated by boiling purified iNOS in EDTA. As analyzed by reverse phase HPLC, this supernatant was a pure solution of a molecule that had the same retention time, tryptic map and partial amino acid sequence as authentic CaM. Thus, it can be concluded that purified iNOS contains CaM.

The possibility that iNOS might contain a covalently embedded CaM-like domain, as does a recently described soybean kinase, Harper, et al., Science 252: 951–954 (1991), was discounted by the nucleic acid and amino acid sequences of iNOS. Moreover, two different procedures abolished the ability of anti-CaM mAb to bind to iNOS in an immunoblot assay, while preserving the reactivity of the mAb with a released protein that comigrated with CaM. Thus, there is no CaM-like epitope intrinsic to iNOS. Instead, the immunologic reactivity of iNOS with anti-CaM mAb was explained by the recovery from pure iNOS of a molecule with the molecular mass, reverse phase HPLC retention time, tryptic map, and amino acid sequence of CaM itself. These data establish that CaM is a noncovalent subunit of iNOS.

It is believed that only three other enzymes bind CaM constitutively, that is, in an apparently $Ca^{++}$-independent manner. These are phosphorylase kinase (Cohen, et al., FEBS Lett. 92: 287–293 [1978]; Picton, et al., Eur. J. Biochem. 111: 553–561[1980]), a cyclic nucleotide phosphodiesterase (Sharma and Wang, J. Biol. Chem. 261: 14160–14166 [1986]), and the adenylyl cyclase of *Bordetella pertussis* (Ladant, J. Biol. Chem. 263: 2612–2618 [1988]). In each case, CaM appears to be dissociated completely by boiling and electrophoresis of the enzyme in SDS. In contrast, iNOS retains a portion of its immunologically detectable CaM under the same conditions. By this criterion, iNOS may bind CaM more tightly than any enzyme yet described. Nonetheless, a substantial amount of CaM is released from pure iNOS upon electrophoresis under denaturing conditions. Previous failures to detect the resulting 16.9 kDa band can be attributed to the inability of conventional silver or amido black staining procedures to reveal CaM.

Mutation studies have shown that CaM can subserve some of its functions in yeast without binding $Ca^{++}$, Geiser, et al., Cell 65: 949–959 (1991), and a CaM-dependent kinase in neuronal cells can become $Ca^{++}$-independent after undergoing phosphorylation (Ikeda, et al., J. Biol. Chem. 266: 11582–11588 (1991). CaM copurifies with iNOS in the absence of added $Ca^{++}$, suggesting that the ability of iNOS to bind CaM is largely $Ca^{++}$-independent.

Calmodulin is a ubiquitous and abundant cytosolic protein in eukaryotes and is probably present in excess over the apoprotein of iNOS. In view of iNOS's high affinity for CaM, CaM is likely to complex with iNOS during or promptly after the translation of iNOS mRNA, even at the low levels of intracellular $Ca^{++}$ characteristic of resting cells (~100 nM). This may explain why iNOS appears to be activated simply by being synthesized. These results suggest that differences in the CaM-binding sequences of iNOS and constitutive NOS (cNOS) have profound consequences for the contrasting modes of activation of these two enzymes, and thus for their physiologic roles.

EXAMPLE 3

Cloning of iNOS cDNA

Two 100-liter cultures of RAW 264.7 (ATCC TIB71) macrophage-like cells were activated for 8–11 h with murine interferon-γ (IFNγ) and bacterial lipopolysaccharide (LPS). Inducible iNOS (3.4 mg) was purified from the cell lysates by anion exchange, nucleotide affinity and size exclusion chromatography according to Example 1. Since standard methods were unable to derive $NH_2$-terminal amino acid sequence from purified iNOS, polyclonal antibody was raised for identifying cloned iNOS. Anti-iNOS antiserum was raised by injecting a rabbit with 90 μg of 130-kDa iNOS that was purified from activated RAW 264.7 cells as described in Example 1 and emulsified with Freund's complete adjuvant. The animal received two booster injections of incomplete Freund's adjuvant containing 45–50 μg each of iNOS that was purified as above and additionally by isolation of the 130-kDa region on SDS-PAGE. Anti-iNOS IgG was purified on immobilized recombinant protein G (Pierce), adsorbed with *E. coli*, and used to screen the cDNA library.

The RAW 264.7 murine macrophage cell line was activated with rIFNγ (100 U/ml; Genentech) and LPS (2 μg/ml) for 4 h. Poly(A)-rich RNA with oligo-dT as a primer was used to prepare a cDNA library in the Uni ZAP-XR unidirectional vector following the manufactur's instructions (Stratagene). The antibody identified 13 clones among $5 \times 10^4$ phages in the cDNA library prepared from the activated RAW 264.7 cells (FIG. 1). The cDNA inserts in these clones contained overlapping portions of the coding region. Clones A1, A2 and B1 included the ATG initiation codon within a consensus initiation sequence (GAC<u>ATG</u>G), Kozak, J. Biol. Chem. 266: 19867–19870 (1991). The 3' untranslated regions of clones A1 and A2 are mutually identical, but differed from the mutually similar 3' untranslanted regions sequenced in clones B1–B11. Clones A1 and A2 encode a protein 22 amino acid residues shorter at the COOH-terminus, whose last 10 amino acid residues differ completely from the COOH-terminus encoded by clones of the B series. This suggests the existence of at least two isoforms of iNOS mRNA, probably generated by alternative splicing. At the protein level, the sequence was confirmed for peptides that corresponded to 22 of the 34 $NH_2$-terminal residues encoded by the clones A1, A2 and B1 but lacking from the B clones; to Arg704 encoded by the B clones; and to 32 residues of the B clones' longer COOH-terminus, but not to the shorter COOH-terminus. Therefore, for the nucleotide and deduced amino acid sequences as shown in FIG. 2, the $NH_2$-terminus is contributed by the A1, A2 and B1 clones, and the rest of the molecule by the remaining B clones, totalling about 1144 amino acids with a predicted molecular mass of about 130,556.

The nucleotide sequence of the short isoform is identical with the long isoform from nucleotide 1 through nucleotide 3591 as depected in FIG. 2. The nucleotide and amino acid sequence of the carboxyl terminus of the short form is shown beginning at nucleotide 3592 and running through 3621, see Table 1. Table 2 depicts the entire carboxyl terminus nucleotide sequence of the short isoform of iNOS.

Samples of the cDNA encoding both isoforms, short and long, have been deposited under the Budapest Treaty in the American Type Culture Collection, 12301 Parklawn Drive, Rockville, Md. 20852, USA. All plasmids are contained in *E. coli* strain DH5α. On Jan. 24, 1992 the plasmid piNOSL1 containing the cDNA encoding the native long form of iNOS was deposited and given accession number 68899. On Jan. 24, 1992 the plasmid piNOS 13 containing cDNA encoding the long isoform of iNOS was deposited and given accession number 68901. On Jan. 24, 1992 the plasmid piNOS 29 containing cDNA encoding the short isoform of iNOS was deposited and given accession number 68901.

EXAMPLE 4

Confirmation of the Amino Acid Sequence of iNOS and Comparison with cNOS

To confirm the deduced amino acid sequence, purified, enzymatically active iNOS (from Example 1) was subjected to reverse phase HPLC on a $C_4$ column, digested with trypsin following standard procedures, and the peptides separated by reverse phase HPLC on a $C_{18}$ column. The fragments recovered in greatest abundance were sequenced by Edman degradation. Eighteen tryptic peptides matched the deduced amino acid sequence, confirmining that the cDNA encoded iNOS. However, only 9% of the predicted amino acid sequence was confirmed in this manner.

Additional confirmation of the amino acid sequence was obtained by liquid chromatography-mass spectrometry (LC-MS). A tryptic digest of iNOS (~20–30 pmol) was separated on a $C_{18}$ packed capillary column and fed directly into the electrospray interface of a quadrupole mass spectrometer. McLuckey et al., Anal. Chem. 63: 375–383 (1991). Peptides were separated on a $C_{18}$ reverse phase packed capillary column (0.5 mm ID) at a flow rate of 2 μl/min using 0.1% aqueous TFA and a gradient of 2–80% acetonitrile over 40 min. The effluent was fed directly to the electrospray interface of a Finnigan MAT TSQ-700 quadrupole mass spectrometer. A total of 743 scans (3 s cycle time) over the range m/z 500–2000 were collected. A plot of the intensity of the most intense ion in each mass spectrum vs. time yielded the base peak chromatogram shown in FIG. 3A. The arrow indicates the peak detailed in (B). With few exceptions electrospray spectra of peptides contain ions only for intact molecules. Nevertheless, the present spectra were quite complex, due to the large number of peptides in the digest and the multiplicity of charge states observed.

FIG. 3B illustrates this with the mass spectrum for one base ion peak. Singly and doubly charged ions were observed for 6 peptides. Five of these differed by <1 mass unit from products expected from tryptic cleavage of the protein deduced from the cDNA sequence. Rarely, an observed mass corresponded to more than one possible tryptic peptide; an example is included in FIG. 3B. The mass spectrum depicted in FIG. 3B is the result of the average of scans 371–377. Ions corresponding to both the +1 and +2 charge states of 6 different peptides are evident. Four of these can be uniquely assigned to predicted products of the tryptic digest of iNOS. The peptide with Mr 1105 has two possible assignments, while the peptide with Mr 1560 did not correspond to a predicted tryptic fragment.

The MacProMass program, Lee and Vemuri, Biomed. Environment. Mass. Spec. 19: 639–645 (1990), was used to calculate values for all expected tryptic peptides, including those resulting from incomplete digestion. Mass chromatograms were generated for each expected mass. For peptides larger than 1000 Da, two or more charge states had to be present in the spectrum before an assignment was made. Because no data were collected for m/z <500, multiply-charged ions smaller than 1000 Da were not observed. Consequently assignments for these peptides had to be based on a single ion in the spectrum. Such assignments were made only if the ion in question could not be included in an ion series corresponding to a larger peptide. Using these criteria, assignments of tryptic peptides were made that confirmed 65% of the deduced amino acid sequence of iNOS. LC-MS analysis of an endopeptidase Asp-N digest extended the confirmation to 78% of the sequence. For these studies, enzymatic digestion of iNOS was carried out without prior reduction and alkylation. Cysteine residues were present in 12 of the 17 regions for which LC-MS did not provide sequence confirmation; these peptides may have been linked together.

The amino acid sequences of iNOS and cNOS were compared. At the amino acid level, mouse macrophage iNOS is only 51% identical to the deduced sequence of rat cerebellar cNOS as described by Bredt et al., Nature 351: 714–718 (1991). Although both enzymes have 24 cysteines, only 16 of them are positionally conserved. With respect to cNOS, iNOS is shorter at the $NH_2$-terminus (222 residues), midportion (52 residues in 5 sites), and COOH-terminus (12 residues); these amino acids are presumably not necessary for catalysis. As for cNOS, the COOH-terminal half of iNOS is homologous to cytochrome P450 reductase (29% identical), an enzyme that also employs FMN, FAD and NADPH as cofactors. Porter and Kasper, Proc. Natl. Acad. Sci. USA 82: 973–977 (1985). The COOH-termini of iNOS and cNOS can be modelled to share regions of multi-stranded β sheet and surrounding α helices that conform to portions of the nucleotide binding domains of crystallographically resolved ferredoxin-NADP$^+$ reductase. By this analysis, iNOS and cNOS share discontinuous residues that are predicted to comprise nucleotide contact sites. These sites overlap only partially with the cofactor binding sites designated by Bredt et al. based on homology analysis of primary structure. Bredt e supra.

Given that the enzymatic activity of iNOS is independent of added calmodulin, Stuehr et al. Proc. Natl. Acad. Sci. USA 88: 7773–7777 (1991) and Yui et al., J. Biol. Chem. 266: 12544–12547 (1991), it was noteworthy that amino acids 501–532 of iNOS consisted almost exclusively of basic and hydrophobic residues characteristic of calmodulin-binding sites, O'Neil and DeGrado, TIBS 15: 59–64 (1990). In contrast to the high homology between iNOS and cNOS in other presumed cofactor-binding sites, this region of iNOS was only 43% identical to the 21 residues designated by Bredt et al. as the presumptive calmodulin-binding site of cNOS.

EXAMPLE 5

Immunologic Induction of iNOS at the Transcriptional Level

The first demonstration that isolated mammalian cells could synthesize inorganic oxides of nitrogen involved macrophages, Stuehr and Marletta, Proc. Natl. Acad. Sci. USA 82: 7738–7742 (1985). Nitrite and nitrate accumulated in the extracellular medium only if the cells were immunologically activated. However, the mechanism by which agents such as IFNγ and LPS enhance the accumulation of nitrite/nitrate has never been established. Induction of iNOS itself is a plausible hypothesis, in that enzyme activity and chromatographically recognizable iNOS protein have only been observed in activated cells. Inducible NOS enzyme activity in lysates of IFNγ- and LPS-activated RAW 264.7 cells was measured as described. No baseline iNOS activity was evident at 0 h and trace activity at 2 h, with a sharp increase at 4 h. Following the addition of actinomycin D (0.2 μg/ml) at 2 h, there was a 40% diminution in the induction of iNOS activity in the next 2 h period. After addition of actinomycin D at time 0, there was 100% inhibition of induction of NOS activity at both 2 h and 4 h. In all sets, recombinant mouse IFNγ (10 ng/ml) and LPS (1 μg/ml) were added at time 0. At each time point, cell viability as determined by trypan blue exclusion exceeded 90%. Western blot analysis of the lysates revealed the following. Aliquots (10 μg protein) of the lysates were electrophoresed in 7.5% SDS-PAGE, electroblotted to nitrocellulose, probed with a 1:1000 dilution of anti-iNOS IgG, and detected with a 1:1000 dilution of alkaline phosphatase-conjugated sheep anti-rabbit IgG (Boehringer-Mannheim). The positive control consisted of lysate from RAW cells activated for 12 h.

mRNA was prepared from RAW cells that were untreated, activated with IFNγ and LPS for 4 h, or activated with IFNγ and LPS for 4 h in the presence of actinomycin D.

After electrophoresis in a 1% agarose gel with formaldehyde and transfer to a nylon membrane the mRNA was hybridized with $^{32}$P-labelled antisense RNA prepared from iNOS clone B2 corresponding to amino acids 35–1144 and the 3' untranslated region. Immunologic activation of RAW cells induced NOS enzyme activity, accumulation of iNOS mRNA (~4.4-kb), and the appearance of iNOS protein, all by an actinomycin D-sensitive process. Likewise, in primary peritoneal macrophages elicited by intraperitoneal injection of thioglycollate broth, iNOS was undetectable by immunofluorescence. Exposure of the cells to IFNγ or LPS induced small amounts of iNOS antigen in ~50% of the cells and larger amounts in occasional cells. Treatment of the cells with IFNγ and LPS in combination induced large amounts of iNOS antigen in ~85% of the cells.

EXAMPLE 6

Relation of Macrophage iNOS to NOS in Other Cell Types

By Western blot, a protein antigenically related to and sharing the same apparent Mr as RAW cell iNOS was readily detected in primary mouse peritoneal macrophages and mammary adenocarcinoma cells, provided they had been exposed to IFNγ and LPS. By Western blot analysis, glycogen-elicited rat peritoneal neutrophils were also reactive, consistent with a report that these cells contain a $Ca^{++}$, calmodulin-independent NOS, Yui, et al., J. Biol. Chem. 266: 3369–3371(1991), although the apparent Mr of the enzyme in the Western blot (~130 kDa) was smaller than that reported for the purified enzyme (150 kDa) as described by Yui et al. Thus, a protein closely related to macrophage iNOS appears to be widely distributed in other activated cell populations. In contrast, anti-iNOS antibody was nonreactive with recombinant rat cerebellar cNOS. The negative result with rat cNOS could not be attributed to a species restriction of the anti-iNOS antibody, given that it reacted with rat neutrophils.

EXAMPLE 7

Production and Activity of Recombinant iNOS

Figure 4:
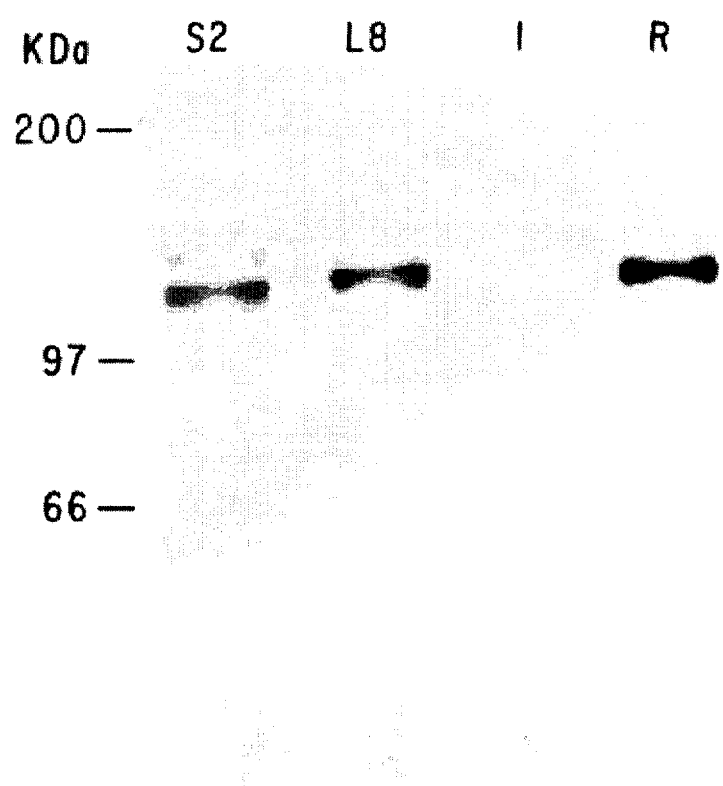
FIG. 4 A Western blot is shown which demonstrates recombinant expression of iNOS in recombinant host cells.

A 3934 base pair HincII-SspI fragment of the long form iNOS cDNA containing the full-length coding region was inserted into the expression vector pCDNAI (Invitrogen Corp.) downstream from the promoter/enhancer region from the immediate early gene of the human cytomegalovirus (CMV) to form the plasmid piNOSL8. Similarly, a 3934 base pair HincII-SspI fragment of the short form iNOS cDNA containing its full-length coding region was inserted into pCDNAI to form piNOSS2. Twenty micrograms of each DNA (piNOSL8, piNOSS2, or the vector pcDNAI) were applied to 293 cells, a human renal epithelial cell line (ATCC CRL 1573) in 100mm culture dishes, and transfected by the calcium phosphate method. After about 14 hours at 37° C. in 5% $CO_2$, the medium was changed and the cells were incubated for an additional 12 hours or more. The culture medium was collected for measurement of the accumulated nitrite, and the cells were harvested to prepare lysates for nitric oxide synthase enzyme assays and for immunoblot using rabbit IgG specific for pure iNOS protein. As a positive control, lysate was prepared from the macrophage-like RAW 264.7 cell line (ATCC TIB 17) after activation by interferon-gamma and bacterial lipopolysaccharide. Twenty micrograms of protein from each lysate were used for a Western blot shown in FIG. 4 (L8—piNOSL8; S2—piNOSS2; I—pcDNAI; RAW—RAW 264.7 cells). FIG. 4 shows that piNOS directed the expression of a protein of the same molecular weight and immunological properties as iNOS from RAW 264.7 cells, whereas piNOSS2 directed expression of a protein of slightly lower molecular weight, as expected. No immunologically reactive band was observed from the pcDNA transfected cells.

The enzymatic activity of the recombinantly produced iNOS was determined by the method of measuring the accumulation of nitrite in the culture medium from transfected cells. As shown in Table 3, cells transfected with piNOSL8 produced a significant amount of nitrite which accumulated in the culture medium. Lysates of cells transfected with piNOSL8 produced significant amounts of nitrite when provided with the known substrates and cofactors of iNOS. These data demonstrate the production of enzymatically active recombinant iNOS.

TABLE 3

Nitrite Accumulation and Activity of Nitric Oxide Synthase from 293 Cells Transfected with Various DNA

| PLASMID | INSERT | ACCUMULATED NITRITE (1) | ACTIVITY OF NOS (2) |
|---|---|---|---|
| pcDNAI | None | 0.0 | 0.00 |
| piNOSl8 | iNOS-long | 223.7 | 0.69* |
| piNOSS2 | iNOS-short | 0.0 | 0.00 |

1 — nmols $NO_2^-/10^7$ cells
2 — (nmols/mg/min)
* — specific activity of NOS in RAW cells treated with interferon-gamma and LPS is usually about 2 nmoles $NO_2^-$/mg protein/min.

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 30 bases
        ( B ) TYPE: nucleic acid ( C ) STRANDEDNESS: single
( D ) TOPOLOGY: linear ( x i ) SEQUENCE DESCRIPTION: SEQ ID NO:1:

| GCCTCGGTCC TCCTCAACCC ACAGAATAAC | 30 |

( 2 ) INFORMATION FOR SEQ ID NO:2:

( i ) SEQUENCE CHARACTERISTICS:
( A ) LENGTH: 10 amino acids
( B ) TYPE: amino acid
( D ) TOPOLOGY: linear ( x i ) SEQUENCE DESCRIPTION: SEQ ID NO:2:

Ala Ser Val Leu Leu Asn Pro Gln Asn Asn
              5                    10

( 2 ) INFORMATION FOR SEQ ID NO:3:

( i ) SEQUENCE CHARACTERISTICS:
( A ) LENGTH: 352 bases
( B ) TYPE: nucleic acid
( C ) STRANDEDNESS: single
( D ) TOPOLOGY: linear ( x i ) SEQUENCE DESCRIPTION: SEQ ID NO:3:

| GGCCTCGGTC CTCCTCAACC CACAGAATAA CTAAGTCCTG | 40 |
| CTGGATGGGA CAGAGTGGCG CCCAGACGTG GGGCTCGAGG | 80 |
| CACAGACCTT TGCCCAGTGG AGACCACGGA GACTAGCTCC | 120 |
| AAGAGAATTT TGTCACGACT AGATGAATAA GCCGTTTGAG | 160 |
| GAATGCTCCT ACTGCTCACT GGAGAAGTTG TTCTCGGTAA | 200 |
| GTTGATTCCT CTCCACTAAG AAATGGGAAC TAGCCAGGTG | 240 |
| GTGGTGGCAC ATGCCTTTAA TCCCAGCACT GGGAGGCAG | 280 |
| AGGCAGGCCG ATTCTACAAA GTGAGTTCCA GGACAGCCAG | 320 |
| GGCTACACAG AGAAACCCTG TCTCAAAAAA TC | 352 |

( 2 ) INFORMATION FOR SEQ ID NO:4:

( i ) SEQUENCE CHARACTERISTICS:
( A ) LENGTH: 4041 bases
( B ) TYPE: nucleic acid
( C ) STRANDEDNESS: single
( D ) TOPOLOGY: linear ( x i ) SEQUENCE DESCRIPTION: SEQ ID NO:4:

| CTGGAGGGGT ATAAATACCT GATGGCTGCT GCCAGGGTCA | 40 |
| CAACTTTACA GGGAGTTGAA GACTGAGACT CTGGCCCCAC | 80 |
| GGGACACAGT GTCACTGGTT TGAAACTTCT CAGCCACCTT | 120 |
| GGTGAAGGGA CTGAGCTGTT AGAGACACTT CTGAGGCTCC | 160 |
| TCACGCTTGG GTCTTGTTCA CTCCACGGAG TAGCCTAGTC | 200 |
| AACTGCAAGA GAACGGAGAA CGTTGGATTT GGAGCAGAAG | 240 |
| TGCAAAGTCT CAGACATGGC TTGCCCCTGG AAGTTTCTCT | 280 |
| TCAAAGTCAA ATCCTACCAA AGTGACCTGA AAGAGGAAAA | 320 |
| GGACATTAAC AACAACGTGA AGAAACCCC TTGTGCTGTT | 360 |
| CTCAGCCCAA CAATACAAGA TGACCCTAAG AGTCACCAAA | 400 |

-continued

| | | | | |
|---|---|---|---|---|
| ATGGCTCCCC | GCAGCTCCTC | ACTGGGACAG | CACAGAATGT | 440 |
| TCCAGAATCC | CTGGACAAGC | TGCATGTGAC | ATCGACCCGT | 480 |
| CCACAGTATG | TGAGGATCAA | AAACTGGGGC | AGTGGAGAGA | 520 |
| TTTTGCATGA | CACTCTTCAC | CACAAGGCCA | CATCGGATTT | 560 |
| CACTTGCAAG | TCCAAGTCTT | GCTTGGGGTC | CATCATGAAC | 600 |
| CCCAAGAGTT | TGACCAGAGG | ACCCAGAGAC | AAGCCTACCC | 640 |
| CTCTGGAGGA | GCTCCTGCCT | CATGCCATTG | AGTTCATCAA | 680 |
| CCAGTATTAT | GGCTCCTTTA | AAGAGGCAAA | AATAGAGGAA | 720 |
| CATCTGGCCA | GGCTGGAAGC | TGTAACAAAG | GAAATAGAAA | 760 |
| CAACAGGAAC | CTACCAGCTC | ACTCTGGATG | AGCTCATCTT | 800 |
| TGCCACCAAG | ATGGCCTGGA | GGAATGCCCC | TCGCTGCATC | 840 |
| GGCAGGATCC | AGTGGTCCAA | CCTGCAGGTC | TTTGACGCTC | 880 |
| GGAACTGTAG | CACAGCACAG | GAAATGTTTC | AGCACATCTG | 920 |
| CAGACACATA | CTTTATGCCA | CCAACAATGG | CAACATCAGG | 960 |
| TCGGCCATCA | CTGTGTTCCC | CCAGCGGAGT | GACGGCAAAC | 1000 |
| ATGACTTCAG | GCTCTGGAAT | TCACAGCTCA | TCCGGTACGC | 1040 |
| TGGCTACCAG | ATGCCCGATG | CACCATCAG | AGGGGATGCT | 1080 |
| GCCACCTTGG | AGTTCACCCA | GTTGTGCATC | GACCTAGGCT | 1120 |
| GGAAGCCCCG | CTATGGCCGC | TTTGATGTGC | TGCCTCTGGT | 1160 |
| CTTGCAAGCT | GATGGTCAAG | ATCCAGAGGT | CTTTGAAATC | 1200 |
| CCTCCTGATC | TTGTGTTGGA | GGTGACCATG | GAGCATCCCA | 1240 |
| AGTACGAGTG | GTTCCAGGAG | CTCGGGTTGA | AGTGGTATGC | 1280 |
| ACTGCCTGCC | GTGGCCAACA | TGCTACTGGA | GGTGGGTGGC | 1320 |
| CTCGAATTCC | CAGCCTGCCC | CTTCAATGGT | TGGTACATGG | 1360 |
| GCACCGAGAT | TGGAGTTCGA | GACTTCTGTG | ACACACAGCG | 1400 |
| CTACAACATC | CTGGAGGAAG | TGGGCCGAAG | GATGGGCCTG | 1440 |
| GAGACCCACA | CACTGGCCTC | CCTCTGGAAA | GACCGGGCTG | 1480 |
| TCACGGAGAT | CAATGTGGCT | GTGCTCCATA | GTTTCCAGAA | 1520 |
| GCAGAATGTG | ACCATCATGG | ACCACCACAC | AGCCTCAGAG | 1560 |
| TCCTTCATGA | AGCACATGCA | GAATGAGTAC | CGGGCCCGTG | 1600 |
| GAGGCTGCCC | GGCAGACTGG | ATTTGGCTGG | TCCCTCCAGT | 1640 |
| GTCTGGGAGC | ATCACCCCTG | TGTTCCACCA | GGAGATGTTG | 1680 |
| AACTATGTCC | TATCTCCATT | CTACTACTAC | CAGATCGAGC | 1720 |
| CCTGGAAGAC | CCACATCTGG | CAGAATGAGA | AGCTGAGGCC | 1760 |
| CAGGAGGAGA | GAGATCCGAT | TTAGAGTCTT | GGTGAAAGTG | 1800 |
| GTGTTCTTTG | CTTCCATGCT | AATGCGAAAG | GTCATGGCTT | 1840 |
| CACGGGTCAG | AGCCACAGTC | CTCTTTGCTA | CTGAGACAGG | 1880 |
| GAAGTCTGAA | GCACTAGCCA | GGGACCTGGC | CACCTTGTTC | 1920 |
| AGCTACGCCT | TCAACACCAA | GGTTGTCTGC | ATGGACCAGT | 1960 |
| ATAAGGCAAG | CACCTTGGAA | GAGGAGCAAC | TACTGCTGGT | 2000 |

| | | | | |
|---|---|---|---|---|
| GGTGACAAGC | ACATTTGGGA | ATGGAGACTG | TCCCAGCAAT | 2040 |
| GGGCAGACTC | TGAAGAAATC | TCTGTTCATG | CTTAGAGAAC | 2080 |
| TCAACCACAC | CTTCAGGTAT | GCTGTGTTTG | GCCTTGGCTC | 2120 |
| CAGCATGTAC | CCTCAGTTCT | GCGCCTTTGC | TCATGACATC | 2160 |
| GACCAGAAGC | TGTCCCACCT | GGGAGCCTCT | CAGCTTGCCC | 2200 |
| CAACAGGAGA | AGGGGACGAA | CTCAGTGGGC | AGGAGGATGC | 2240 |
| CTTCCGCAGC | TGGGCTGTAC | AAACCTTCCG | GGCAGCCTGT | 2280 |
| GAGACCTTTG | ATGTCCGAAG | CAAACATCAC | ATTCAGATCC | 2320 |
| CGAAACGCTT | CACTTCCAAT | GCAACATGGG | AGCCACAGCA | 2360 |
| ATATAGGCTC | ATCCAGAGCC | GGAGCCTTT | AGACCTCAAC | 2400 |
| AGAGCCCTCA | GCAGCATCCA | TGCAAAGAAC | GTGTTTACCA | 2440 |
| TGAGGCTGAA | ATCCAGCAG | AATCTGCAGA | GTGAAAAGTC | 2480 |
| CAGCCGCACC | ACCCTCCTCG | TTCAGCTCAC | CTTCGAGGGC | 2520 |
| AGCCGAGGGC | CCAGCTACCT | GCCTGGGGAA | CACCTGGGGA | 2560 |
| TCTTCCCAGG | CAACCAGACC | GCCCTGGTGC | AGGGAATCTT | 2600 |
| GGAGCGAGTT | GTGGATTGTC | CTACACCACA | CCAAACTGTG | 2640 |
| TGCCTGGAGG | TTCTGGATGA | GAGCGGCAGC | TACTGGGTCA | 2680 |
| AAGACAAGAG | GCTGCCCCCC | TGCTCACTCA | GCCAAGCCCT | 2720 |
| CACCTACTTC | CTGGACATTA | CGACCCCTCC | CACCCAGCTG | 2760 |
| CAGCTCCACA | AGCTGGCTCG | CTTTGCCACG | GACGAGACGG | 2800 |
| ATAGGCAGAG | ATTGGAGGCC | TTGTGTCAGC | CCTCAGAGTA | 2840 |
| CAATGACTGG | AAGTTCAGCA | ACAACCCCAC | GTTCCTGGAG | 2880 |
| GTGCTTGAAG | AGTTCCCTTC | CTTGCATGTG | CCCGCTGCCT | 2920 |
| TCCTGCTGTC | GCAGCTCCCT | ATCTTGAAGC | CCCGCTACTA | 2960 |
| CTCCATCAGC | TCCTCCCAGG | ACCACACCCC | CTCGGAGGTT | 3000 |
| CACCTCACTG | TGGCCGTGGT | CACCTACCGC | ACCCGAGATG | 3040 |
| GTCAGGGTCC | CCTGCACCAT | GGTGTCTGCA | GCACTTGGAT | 3080 |
| CAGGAACCTG | AAGCCCCAGG | ACCCAGTGCC | CTGCTTTGTG | 3120 |
| CGAAGTGTCA | GTGGCTTCCA | GCTCCCTGAG | GACCCCTCCC | 3160 |
| AGCCTTGCAT | CCTCATTGGG | CCTGGTACGG | GCATTGCTCC | 3200 |
| CTTCCGAAGT | TTCTGGCAGC | AGCGGCTCCA | TGACTCCCAG | 3240 |
| CACAAAGGGC | TCAAAGGAGG | CCGCATGAGC | TTGGTGTTTG | 3280 |
| GGTGCCGGCA | CCCGGAGGAG | GACCACCTCT | ATCAGGAAGA | 3320 |
| AATGCAGGAG | ATGGTCCGCA | AGAGAGTGCT | GTTCCAGGTG | 3360 |
| CACACAGGCT | ACTCCCGGCT | GCCCGGCAAA | CCCAAGGTCT | 3400 |
| ACGTTCAGGA | CATCCTGCAA | AAGCAGCTGG | CCAATGAGGT | 3440 |
| ACTCAGCGTG | CTCCACGGGG | AGCAGGGCCA | CCTCTACATT | 3480 |
| TGCGGAGATG | TGCGCATGGC | TCGGGATGTG | GCTACCACAT | 3520 |
| TGAAGAAGCT | GGTGGCCACC | AAGCTGAACT | TGAGCGAGGA | 3560 |
| GCAGGTGGAA | GACTATTTCT | TCCAGCTCAA | GAGCCAGAAA | 3600 |

-continued

```
CGTTATCATG AAGATATCTT CGGTGCAGTC TTTTCCTATG                    3640

GGGCAAAAAA GGGCAGCGCC TTGGAGGAGC CCAAAGCCAC                    3680

GAGGCTCTGA CAGCCCAGAG TTCCAGCTTC TGGCACTGAG                    3720

TAAAGATAAT GGTGAGGGGC TTGGGGAGAC AGCGAAATGC                    3760

AATCCCCCCC AGCTCCCTCC TTCTCCTTCT CCTCCTTTGC                    3800

CTCTCACTCT TCCTTGGAGC TGAGAGCAGA GAAAAACTCA                    3840

ACCTCCTGAC TGAAGCACTT TGGGTGACCA CCAGGAGGCA                    3880

CCATGCCGCC GCTCTAATAC TTAGCTGCAC TATGTACAGA                    3920

TATTTATACT TCATATTTAA GAAAACAGAT ACTTTGTCT                     3960

ACTCCCAATG ATGGCTTGGG CCTTTCCTGT ATAATTCCTT                    4000

GATGAAAAAT ATTTATATAA AATACATTTT ATTTTAATCA                    4040

C                                                             4041
```

( 2 ) INFORMATION FOR SEQ ID NO:5:

( i ) SEQUENCE CHARACTERISTICS:
        ( A ) LENGTH: 1144 amino acids
        ( B ) TYPE: amino acid
        ( D ) TOPOLOGY: linear ( x i ) SEQUENCE DESCRIPTION: SEQ ID NO:5:

```
Met Ala Cys Pro Trp Lys Phe Leu Phe Lys Val Lys Ser Tyr Gln
              5                  10                     15

Ser Asp Leu Lys Glu Glu Lys Asp Ile Asn Asn Val Lys Lys
              20                 25                     30

Thr Pro Cys Ala Val Leu Ser Pro Thr Ile Gln Asp Asp Pro Lys
              35                 40                     45

Ser His Gln Asn Gly Ser Pro Gln Leu Leu Thr Gly Thr Ala Gln
              50                 55                     60

Asn Val Pro Glu Ser Leu Asp Lys Leu His Val Thr Ser Thr Arg
              65                 70                     75

Pro Gln Tyr Val Arg Ile Lys Asn Trp Gly Ser Gly Glu Ile Leu
              80                 85                     90

His Asp Thr Leu His His Lys Ala Thr Ser Asp Phe Thr Cys Lys
              95                 100                    105

Ser Lys Ser Cys Leu Gly Ser Ile Met Asn Pro Lys Ser Leu Thr
              110                115                    120
Arg Gly Pro Arg Asp Lys Pro Thr Pro Leu Glu Glu Leu Leu Pro
              125                130                    135

His Ala Ile Glu Phe Ile Asn Gln Tyr Tyr Gly Ser Phe Lys Glu
              140                145                    150

Ala Lys Ile Glu Glu His Leu Ala Arg Leu Glu Ala Val Thr Lys
              155                160                    165

Glu Ile Glu Thr Thr Gly Thr Tyr Gln Leu Thr Leu Asp Glu Leu
              170                175                    180

Ile Phe Ala Thr Lys Met Ala Trp Arg Asn Ala Pro Arg Cys Ile
              185                190                    195

Gly Arg Ile Gln Trp Ser Asn Leu Gln Val Phe Asp Ala Arg Asn
              200                205                    210

Cys Ser Thr Ala Gln Glu Met Phe Gln His Ile Cys Arg His Ile
              215                220                    225

Leu Tyr Ala Thr Asn Asn Gly Asn Ile Arg Ser Ala Ile Thr Val
              230                235                    240
```

| | | | | | | | | | | | | |
|---|---|---|---|---|---|---|---|---|---|---|---|---|
|Phe|Pro|Gln|Arg|Ser 245|Asp|Gly|Lys|His 250|Asp|Phe|Arg|Leu|Trp|Asn 255|
|Ser|Gln|Leu|Ile|Arg 260|Tyr|Ala|Gly|Tyr 265|Gln|Met|Pro|Asp|Gly|Thr 270|
|Ile|Arg|Gly|Asp|Ala 275|Ala|Thr|Leu|Glu 280|Phe|Thr|Gln|Leu|Cys|Ile 285|
|Asp|Leu|Gly|Trp|Lys 290|Pro|Arg|Tyr|Gly 295|Arg|Phe|Asp|Val|Leu|Pro 300|
|Leu|Val|Leu|Gln|Ala 305|Asp|Gly|Gln|Asp 310|Pro|Glu|Val|Phe|Glu|Ile 315|
|Pro|Pro|Asp|Leu|Val 320|Leu|Glu|Val|Thr 325|Met|Glu|His|Pro|Lys|Tyr 330|
|Glu|Trp|Phe|Gln|Glu 335|Leu|Gly|Leu|Lys 340|Trp|Tyr|Ala|Leu|Pro|Ala 345|
|Val|Ala|Asn|Met|Leu 350|Leu|Glu|Val|Gly 355|Gly|Leu|Glu|Phe|Pro|Ala 360|
|Cys|Pro|Phe|Asn|Gly 265|Trp|Tyr|Met|Gly 370|Thr|Glu|Ile|Gly|Val|Arg 375|
|Asp|Phe|Cys|Asp|Thr 380|Gln|Arg|Tyr|Asn 385|Ile|Leu|Glu|Glu|Val|Gly 390|
|Arg|Arg|Met|Gly|Leu 395|Glu|Thr|His|Thr 400|Leu|Ala|Ser|Leu|Trp|Lys 405|
|Asp|Arg|Ala|Val|Thr 410|Glu|Ile|Asn|Val 415|Ala|Val|Leu|His|Ser|Phe 420|
|Gln|Lys|Gln|Asn|Val 425|Thr|Ile|Met|Asp 430|His|His|Thr|Ala|Ser|Glu 435|
|Ser|Phe|Met|Lys|His 440|Met|Gln|Asn|Glu 445|Tyr|Arg|Ala|Arg|Gly|Gly 450|
|Cys|Pro|Ala|Asp|Trp 455|Ile|Trp|Leu|Val 460|Pro|Pro|Val|Ser|Gly|Ser 465|
|Ile|Thr|Pro|Val|Phe 470|His|Gln|Glu|Met 475|Leu|Asn|Tyr|Val|Leu|Ser 480|
|Pro|Phe|Tyr|Tyr|Tyr 485|Gln|Ile|Glu|Pro 490|Trp|Lys|Thr|His|Ile|Trp 495|
|Gln|Asn|Glu|Lys|Leu 500|Arg|Pro|Arg|Arg 505|Arg|Glu|Ile|Arg|Phe|Arg 510|
|Val|Leu|Val|Lys|Val 515|Val|Phe|Phe|Ala 520|Ser|Met|Leu|Met|Arg|Lys 525|
|Val|Met|Ala|Ser|Arg 530|Val|Arg|Ala|Thr 535|Val|Leu|Phe|Ala|Thr|Glu 540|
|Thr|Gly|Lys|Ser|Glu 545|Ala|Leu|Ala|Arg 550|Asp|Leu|Ala|Thr|Leu|Phe 555|
|Ser|Tyr|Ala|Phe|Asn 560|Thr|Lys|Val|Val 565|Cys|Met|Asp|Gln|Tyr|Lys 570|
|Ala|Ser|Thr|Leu|Glu 575|Glu|Glu|Gln|Leu 580|Leu|Leu|Val|Val|Thr|Ser 585|
|Thr|Phe|Gly|Asn|Gly 590|Asp|Cys|Pro|Ser 595|Asn|Gly|Gln|Thr|Leu|Lys 600|
|Lys|Ser|Leu|Phe|Met 605|Leu|Arg|Glu|Leu 610|Asn|His|Thr|Phe|Arg|Tyr 615|
|Ala|Val|Phe|Gly|Leu 620|Gly|Ser|Ser|Met 625|Tyr|Pro|Gln|Phe|Cys|Ala 630|
|Phe|Ala|His|Asp|Ile|Asp|Gln|Lys|Leu|Ser|His|Leu|Gly|Ala|Ser|

-continued

```
                          635                         640                         645
Gln  Leu  Ala  Pro  Thr  Gly  Glu  Gly  Asp  Glu  Leu  Ser  Gly  Gln  Glu
                     650                      655                         660
Asp  Ala  Phe  Arg  Ser  Trp  Ala  Val  Gln  Thr  Phe  Arg  Ala  Ala  Cys
                     665                      670                         675
Glu  Thr  Phe  Asp  Val  Arg  Ser  Lys  His  His  Ile  Gln  Ile  Pro  Lys
                     680                      685                         690
Arg  Phe  Thr  Ser  Asn  Ala  Thr  Trp  Glu  Pro  Gln  Gln  Tyr  Arg  Leu
                     695                      700                         705
Ile  Gln  Ser  Pro  Glu  Pro  Leu  Asp  Leu  Asn  Arg  Ala  Leu  Ser  Ser
                     710                      715                         720
Ile  His  Ala  Lys  Asn  Val  Phe  Thr  Met  Arg  Leu  Lys  Ser  Gln  Gln
                     725                      730                         735
Asn  Leu  Gln  Ser  Glu  Lys  Ser  Ser  Arg  Thr  Thr  Leu  Leu  Val  Gln
                     740                      745                         750
Leu  Thr  Phe  Glu  Gly  Ser  Arg  Gly  Pro  Ser  Tyr  Leu  Pro  Gly  Glu
                     755                      760                         765
His  Leu  Gly  Ile  Phe  Pro  Gly  Asn  Gln  Thr  Ala  Leu  Val  Gln  Gly
                     770                      775                         780
Ile  Leu  Glu  Arg  Val  Val  Asp  Cys  Pro  Thr  Pro  His  Gln  Thr  Val
                     785                      790                         795
Cys  Leu  Glu  Val  Leu  Asp  Glu  Ser  Gly  Ser  Tyr  Trp  Val  Lys  Asp
                     800                      805                         810
Lys  Arg  Leu  Pro  Pro  Cys  Ser  Leu  Ser  Gln  Ala  Leu  Thr  Tyr  Phe
                     815                      820                         825
Leu  Asp  Ile  Thr  Thr  Pro  Pro  Thr  Gln  Leu  Gln  Leu  His  Lys  Leu
                     830                      835                         840
Ala  Arg  Phe  Ala  Thr  Asp  Glu  Thr  Asp  Arg  Gln  Arg  Leu  Glu  Ala
                     845                      850                         855
Leu  Cys  Gln  Pro  Ser  Glu  Tyr  Asn  Asp  Trp  Lys  Phe  Ser  Asn  Asn
                     860                      865                         870
Pro  Thr  Phe  Leu  Glu  Val  Leu  Glu  Glu  Phe  Pro  Ser  Leu  His  Val
                     875                      880                         885
Pro  Ala  Ala  Phe  Leu  Leu  Ser  Gln  Leu  Pro  Ile  Leu  Lys  Pro  Arg
                     890                      895                         900
Tyr  Tyr  Ser  Ile  Ser  Ser  Ser  Gln  Asp  His  Thr  Pro  Ser  Glu  Val
                     905                      910                         915
His  Leu  Thr  Val  Ala  Val  Val  Thr  Tyr  Arg  Thr  Arg  Asp  Gly  Gln
                     920                      925                         930
Gly  Pro  Leu  His  His  Gly  Val  Cys  Ser  Thr  Trp  Ile  Arg  Asn  Leu
                     935                      940                         945
Lys  Pro  Gln  Asp  Pro  Val  Pro  Cys  Phe  Val  Arg  Ser  Val  Ser  Gly
                     950                      955                         960
Phe  Gln  Leu  Pro  Glu  Asp  Pro  Ser  Gln  Pro  Cys  Ile  Leu  Ile  Gly
                     965                      970                         975
Pro  Gly  Thr  Gly  Ile  Ala  Pro  Phe  Arg  Ser  Phe  Trp  Gln  Gln  Arg
                     980                      985                         990
Leu  His  Asp  Ser  Gln  His  Lys  Gly  Leu  Lys  Gly  Gly  Arg  Met  Ser
                     995                      1000                        1005
Leu  Val  Phe  Gly  Cys  Arg  His  Pro  Glu  Glu  Asp  His  Leu  Tyr  Gln
                     1010                     1015                        1020
Glu  Glu  Met  Gln  Glu  Met  Val  Arg  Lys  Arg  Val  Leu  Phe  Gln  Val
                     1025                     1030                        1035
```

| His Thr Gly Tyr | Ser Arg Leu Pro | Gly Lys Pro Lys | Val Tyr Val |
| --- | --- | --- | --- |
| | 1040 | 1045 | 1050 |

| Gln Asp Ile Leu | Gln Lys Gln Leu | Ala Asn Glu Val | Leu Ser Val |
| --- | --- | --- | --- |
| | 1055 | 1060 | 1065 |

| Leu His Gly Glu | Gln Gly His Leu | Tyr Ile Cys Gly | Asp Val Arg |
| --- | --- | --- | --- |
| | 1070 | 1075 | 1080 |

| Met Ala Arg Asp | Val Ala Thr Thr | Leu Lys Lys Leu | Val Ala Thr |
| --- | --- | --- | --- |
| | 1085 | 1090 | 1095 |

| Lys Leu Asn Leu | Ser Glu Glu Gln | Val Glu Asp Tyr | Phe Phe Gln |
| --- | --- | --- | --- |
| | 1100 | 1105 | 1110 |

| Leu Lys Ser Gln | Lys Arg Tyr His | Glu Asp Ile Phe | Gly Ala Val |
| --- | --- | --- | --- |
| | 1115 | 1120 | 1125 |

| Phe Ser Tyr Gly | Ala Lys Lys Gly | Ser Ala Leu Glu | Glu Pro Lys |
| --- | --- | --- | --- |
| | 1130 | 1135 | 1140 |

Ala Thr Arg Leu ( 2 ) INFORMATION FOR SEQ ID NO:6:

( i ) SEQUENCE CHARACTERISTICS:
        ( A ) LENGTH: 4165 bases
        ( B ) TYPE: nucleic acid
        ( C ) STRANDEDNESS: single
        ( D ) TOPOLOGY: linear ( x i ) SEQUENCE DESCRIPTION: SEQ ID NO:6:

| | | | | |
| --- | --- | --- | --- | --- |
| CTGGAGGGGT | ATAAATACCT | GATGGCTGCT | GCCAGGGTCA | 40 |
| CAACTTTACA | GGGAGTTGAA | GACTGAGACT | CTGGCCCCAC | 80 |
| GGGACACAGT | GTCACTGGTT | TGAAACTTCT | CAGCCACCTT | 120 |
| GGTGAAGGGA | CTGAGCTGTT | AGAGACACTT | CTGAGGCTCC | 160 |
| TCACGCTTGG | GTCTTGTTCA | CTCCACGGAG | TAGCCTAGTC | 200 |
| AACTGCAAGA | GAACGGAGAA | CGTTGGATTT | GGAGCAGAAG | 240 |
| TGCAAAGTCT | CAGACATGGC | TTGCCCCTGG | AAGTTTCTCT | 280 |
| TCAAAGTCAA | ATCCTACCAA | AGTGACCTGA | AAGAGGAAAA | 320 |
| GGACATTAAC | AACAACGTGA | AGAAAACCCC | TTGTGCTGTT | 360 |
| CTCAGCCCAA | CAATACAAGA | TGACCCTAAG | AGTCACCAAA | 400 |
| ATGGCTCCCC | GCAGCTCCTC | ACTGGGACAG | CACAGAATGT | 440 |
| TCCAGAATCC | CTGGACAAGC | TGCATGTGAC | ATCGACCCGT | 480 |
| CCACAGTATG | TGAGGATCAA | AAACTGGGGC | AGTGGAGAGA | 520 |
| TTTTGCATGA | CACTCTTCAC | CACAAGGCCA | CATCGGATTT | 560 |
| CACTTGCAAG | TCCAAGTCTT | GCTTGGGGTC | CATCATGAAC | 600 |
| CCCAAGAGTT | TGACCAGAGG | ACCCAGAGAC | AAGCCTACCC | 640 |
| CTCTGGAGGA | GCTCCTGCCT | CATGCCATTG | AGTTCATCAA | 680 |
| CCAGTATTAT | GGCTCCTTTA | AAGAGGCAAA | AATAGAGGAA | 720 |
| CATCTGGCCA | GGCTGGAAGC | TGTAACAAAG | GAAATAGAAA | 760 |
| CAACAGGAAC | CTACCAGCTC | ACTCTGGATG | AGCTCATCTT | 800 |
| TGCCACCAAG | ATGGCCTGGA | GGAATGCCCC | TCGCTGCATC | 840 |
| GGCAGGATCC | AGTGGTCCAA | CCTGCAGGTC | TTTGACGCTC | 880 |
| GGAACTGTAG | CACAGCACAG | GAAATGTTTC | AGCACATCTG | 920 |

| | | | |
|---|---|---|---|
| CAGACACATA | CTTTATGCCA | CCAACAATGG | CAACATCAGG | 960 |
| TCGGCCATCA | CTGTGTTCCC | CCAGCGGAGT | GACGGCAAAC | 1000 |
| ATGACTTCAG | GCTCTGGAAT | TCACAGCTCA | TCCGGTACGC | 1040 |
| TGGCTACCAG | ATGCCCGATG | GCACCATCAG | AGGGGATGCT | 1080 |
| GCCACCTTGG | AGTTCACCCA | GTTGTGCATC | GACCTAGGCT | 1120 |
| GGAAGCCCCG | CTATGGCCGC | TTTGATGTGC | TGCCTCTGGT | 1160 |
| CTTGCAAGCT | GATGGTCAAG | ATCCAGAGGT | CTTTGAAATC | 1200 |
| CCTCCTGATC | TTGTGTTGGA | GGTGACCATG | GAGCATCCCA | 1240 |
| AGTACGAGTG | GTTCCAGGAG | CTCGGGTTGA | AGTGGTATGC | 1280 |
| ACTGCCTGCC | GTGGCCAACA | TGCTACTGGA | GGTGGGTGGC | 1320 |
| CTCGAATTCC | CAGCCTGCCC | CTTCAATGGT | TGGTACATGG | 1360 |
| GCACCGAGAT | TGGAGTTCGA | GACTTCTGTG | ACACACAGCG | 1400 |
| CTACAACATC | CTGGAGGAAG | TGGGCCGAAG | GATGGGCCTG | 1440 |
| GAGACCCACA | CACTGGCCTC | CCTCTGGAAA | GACCGGGCTG | 1480 |
| TCACGGAGAT | CAATGTGGCT | GTGCTCCATA | GTTTCCAGAA | 1520 |
| GCAGAATGTG | ACCATCATGG | ACCACCACAC | AGCCTCAGAG | 1560 |
| TCCTTCATGA | AGCACATGCA | GAATGAGTAC | CGGGCCCGTG | 1600 |
| GAGGCTGCCC | GGCAGACTGG | ATTTGGCTGG | TCCCTCCAGT | 1640 |
| GTCTGGGAGC | ATCACCCCTG | TGTTCCACCA | GGAGATGTTG | 1680 |
| AACTATGTCC | TATCTCCATT | CTACTACTAC | CAGATCGAGC | 1720 |
| CCTGGAAGAC | CCACATCTGG | CAGAATGAGA | AGCTGAGGCC | 1760 |
| CAGGAGGAGA | GAGATCCGAT | TTAGAGTCTT | GGTGAAAGTG | 1800 |
| GTGTTCTTTG | CTTCCATGCT | AATGCGAAAG | GTCATGGCTT | 1840 |
| CACGGGTCAG | AGCCACAGTC | CTCTTTGCTA | CTGAGACAGG | 1880 |
| GAAGTCTGAA | GCACTAGCCA | GGGACCTGGC | CACCTTGTTC | 1920 |
| AGCTACGCCT | TCAACACCAA | GGTTGTCTGC | ATGGACCAGT | 1960 |
| ATAAGGCAAG | CACCTTGGAA | GAGGAGCAAC | TACTGCTGGT | 2000 |
| GGTGACAAGC | ACATTTGGGA | ATGGAGACTG | TCCCAGCAAT | 2040 |
| GGGCAGACTC | TGAAGAAATC | TCTGTTCATG | CTTAGAGAAC | 2080 |
| TCAACCACAC | CTTCAGGTAT | GCTGTGTTTG | GCCTTGGCTC | 2120 |
| CAGCATGTAC | CCTCAGTTCT | GCGCCTTTGC | TCATGACATC | 2160 |
| GACCAGAAGC | TGTCCCACCT | GGGAGCCTCT | CAGCTTGCCC | 2200 |
| CAACAGGAGA | AGGGACGAA | CTCAGTGGGC | AGGAGGATGC | 2240 |
| CTTCCGCAGC | TGGGCTGTAC | AAACCTTCCG | GGCAGCCTGT | 2280 |
| GAGACCTTTG | ATGTCCGAAG | CAAACATCAC | ATTCAGATCC | 2320 |
| CGAAACGCTT | CACTTCCAAT | GCAACATGGG | AGCCACAGCA | 2360 |
| ATATAGGCTC | ATCCAGAGCC | CGGAGCCTTT | AGACCTCAAC | 2400 |
| AGAGCCCTCA | GCAGCATCCA | TGCAAAGAAC | GTGTTTACCA | 2440 |
| TGAGGCTGAA | ATCCCAGCAG | AATCTGCAGA | GTGAAAAGTC | 2480 |
| CAGCCGCACC | ACCCTCCTCG | TTCAGCTCAC | CTTCGAGGGC | 2520 |

| | | | | |
|---|---|---|---|---|
| AGCCGAGGGC | CCAGCTACCT | GCCTGGGGAA | CACCTGGGGA | 2560 |
| TCTTCCCAGG | CAACCAGACC | GCCCTGGTGC | AGGGAATCTT | 2600 |
| GGAGCGAGTT | GTGGATTGTC | CTACACCACA | CCAAACTGTG | 2640 |
| TGCCTGGAGG | TTCTGGATGA | GAGCGGCAGC | TACTGGGTCA | 2680 |
| AAGACAAGAG | GCTGCCCCCC | TGCTCACTCA | GCCAAGCCCT | 2720 |
| CACCTACTTC | CTGGACATTA | CGACCCCTCC | CACCCAGCTG | 2760 |
| CAGCTCCACA | AGCTGGCTCG | CTTTGCCACG | GACGAGACGG | 2800 |
| ATAGGCAGAG | ATTGGAGGCC | TTGTGTCAGC | CCTCAGAGTA | 2840 |
| CAATGACTGG | AAGTTCAGCA | ACAACCCCAC | GTTCCTGGAG | 2880 |
| GTGCTTGAAG | AGTTCCCTTC | CTTGCATGTG | CCCGCTGCCT | 2920 |
| TCCTGCTGTC | GCAGCTCCCT | ATCTTGAAGC | CCGCTACTA | 2960 |
| CTCCATCAGC | TCCTCCCAGG | ACCACACCCC | CTCGGAGGTT | 3000 |
| CACCTCACTG | TGGCCGTGGT | CACCTACCGC | ACCCGAGATG | 3040 |
| GTCAGGGTCC | CCTGCACCAT | GGTGTCTGCA | GCACTTGGAT | 3080 |
| CAGGAACCTG | AAGCCCAGG | ACCCAGTGCC | CTGCTTTGTG | 3120 |
| CGAAGTGTCA | GTGGCTTCCA | GCTCCCTGAG | GACCCCTCCC | 3160 |
| AGCCTTGCAT | CCTCATTGGG | CCTGGTACGG | GCATTGCTCC | 3200 |
| CTTCCGAAGT | TTCTGGCAGC | AGCGGCTCCA | TGACTCCCAG | 3240 |
| CACAAGGGC | TCAAAGGAGG | CCGCATGAGC | TTGGTGTTTG | 3280 |
| GGTGCCGGCA | CCCGGAGGAG | GACCACCTCT | ATCAGGAAGA | 3320 |
| AATGCAGGAG | ATGGTCCGCA | AGAGAGTGCT | GTTCCAGGTG | 3360 |
| CACACAGGCT | ACTCCCGGCT | GCCCGGCAAA | CCCAAGGTCT | 3400 |
| ACGTTCAGGA | CATCCTGCAA | AAGCAGCTGG | CCAATGAGGT | 3440 |
| ACTCAGCGTG | CTCCACGGGG | AGCAGGGCCA | CCTCTACATT | 3480 |
| TGCGGAGATG | TGCGCATGGC | TCGGGATGTG | GCTACCACAT | 3520 |
| TGAAGAAGCT | GGTGGCCACC | AAGCTGAACT | TGAGCGAGGA | 3560 |
| GCAGGTGGAA | GACTATTTCT | TCCAGCTCAA | GAGCCAGAAA | 3600 |
| CGTTATCATG | AAGATATCTT | CGGTGCAGTC | TTTTCCTATG | 3640 |
| GGGCAAAAAA | GGGCAGCGCC | TTGGAGGAGC | CCAAAGCCAC | 3680 |
| GAGGCTCTGA | CAGCCCAGAG | TTCCAGCTTC | TGGCACTGAG | 3720 |
| TAAAGATAAT | GGTGAGGGGC | TTGGGGAGAC | AGCGAAATGC | 3760 |
| AATCCCCCCC | AAGCCCCTCA | TGTCATTCCC | CCCTCCTCCA | 3800 |
| CCCTACCAAG | TAGTATTGTA | CTATTGTGGA | CTACTAAATC | 3840 |
| TCTCTCCTCT | CCTCCCTCCC | CTCTCTCCCT | TTCCTCCCTT | 3880 |
| CTTCTCCACT | CCCCAGCTCC | CTCCTTCTCC | TTCTCCTCCT | 3920 |
| TTGCCTCTCA | CTCTTCCTTG | GAGCTGAGAG | CAGAGAAAAA | 3960 |
| CTCAACCTCC | TGACTGAAGC | ACTTTGGGTG | ACCACCAGGA | 4000 |
| GGCACCATGC | CGCCGCTCTA | ATACTTAGCT | GCACTATGTA | 4040 |
| CAGATATTTA | TACTTCATAT | TTAAGAAAAC | AGATACTTTT | 4080 |
| GTCTACTCCC | AATGATGGCT | TGGGCCTTTC | CTGTATAATT | 4120 |

| | |
|---|---|
| CCTTGATGAA AAATATTTAT ATAAAATACA TTTTATTTTA | 4160 |
| ATCAC | 4165 |

What is claimed is:

1. An isolated and purified DNA molecule encoding inducible nitric oxide synthase comprising a nucleotide sequence as set forth in SEQ.ID.No.:6, said DNA molecule encoding a 1144 amino acid inducible nitric oxide synthase.

2. An expression vector containing the DNA molecule of claim 1.

3. A recombinant host cell containing the expression vector of claim 2.

4. A process for producing biologically active recombinant inducible nitric oxide synthase comprising culturing the host cells of claim 3 under conditions suitable for expression of inducible nitric oxide synthase.

5. An isolated and purified DNA molecule encoding inducible nitric oxide synthase comprising a nucleotide sequence as set forth in SEQ.ID.No.: 4, said DNA molecule encoding a 1144 amino acid inducible nitric oxide synthase.

6. An expression vector containing the DNA molecule of claim 5.

7. A recombinant host cell containing the expression vector of claim 6.

8. A process for producing biologically active recombinant inducible nitric oxide synthase comprising culturing the host cells of claim 7 under conditions suitable for expression of inducible nitric oxide synthase.

* * * * *